US012594294B2

(12) United States Patent
Miyazono et al.

(10) Patent No.: US 12,594,294 B2
(45) Date of Patent: Apr. 7, 2026

(54) THERAPEUTIC AND PROPHYLACTIC AGENT FOR GLIOMA, BRAIN TUMOR MALIGNANCY MARKER, BRAIN TUMOR PROGNOSTIC MARKER, METHOD FOR DETERMINING MALIGNANCY AND PROGNOSIS OF BRAIN TUMOR AND ANTIBODY INHIBITING TUMOR PROLIFERATION

(71) Applicants: The University of Tokyo, Tokyo (JP); Yamaguchi University, Yamaguchi (JP)

(72) Inventors: Kohei Miyazono, Tokyo (JP); Ryo Tanabe, Tokyo (JP); Masato Morikawa, Tokyo (JP); Carl-Henrik Heldin, Tokyo (JP); Bengt Westermark, Tokyo (JP); Koji Tamada, Yamaguchi (JP)

(73) Assignees: The University of Tokyo, Tokyo (JP); Yamaguchi University, Yamaguchi (JP)

( * ) Notice: Subject to any disclaimer, the term of this patent is extended or adjusted under 35 U.S.C. 154(b) by 1233 days.

(21) Appl. No.: 17/419,154

(22) PCT Filed: Dec. 27, 2019

(86) PCT No.: PCT/JP2019/051635
§ 371 (c)(1),
(2) Date: Sep. 9, 2021

(87) PCT Pub. No.: WO2020/138503
PCT Pub. Date: Jul. 2, 2020

(65) Prior Publication Data
US 2022/0105122 A1     Apr. 7, 2022

(30) Foreign Application Priority Data
Dec. 28, 2018     (JP) ................................ 2018-248465

(51) Int. Cl.
*C07K 16/18*     (2006.01)
*A61K 31/7088*     (2006.01)
*A61P 35/00*     (2006.01)
*G01N 33/574*     (2006.01)

(52) U.S. Cl.
CPC .......... *A61K 31/7088* (2013.01); *A61P 35/00* (2018.01); *C07K 16/18* (2013.01); *G01N 33/57484* (2013.01)

(58) Field of Classification Search
None
See application file for complete search history.

(56) References Cited

U.S. PATENT DOCUMENTS

2005/0065326 A1     3/2005     Rosen et al.
2010/0167999 A1     7/2010     Vescovi et al.
2010/0196386 A1     8/2010     Olive et al.

FOREIGN PATENT DOCUMENTS

CN          102653783 A       9/2012
CN          108785658 A       11/2018
JP          2009-502771        1/2009
JP          2011-521887        7/2011
WO        WO 03/086301 A2    10/2003
WO        WO 2013045707 A2    4/2013

OTHER PUBLICATIONS

Deshayes et al., "Abnormal production of the TNF-homologue APRIL increases the proliferation of human malignant glioblastoma cell lines via a specific receptor", Oncogene, 23(17):3005-12 (2004).
International Preliminary Report on Patentability in International Application No. PCT/JP2019/051635, issued on Jun. 16, 2021.
Ming-Zhi et al., "Immune checkpoint molecule herpes virus entry mediator is overexpressed and associated with poor prognosis in human glioblastoma", EBioMedicine 43: 159-170 (2019).
Savary et al., "Snail depletes the tumorigenic potential of glioblastoma", Oncogene, 32:5409-5420 (2013).
Torres-Martin et al., "TNF-pathway upregulation in glioblastoma multiforme", Neuro-Oncology, 14, p. iii48, p. 122 (2012).
Office Action issued in Chinese Application No. 201980092527.2, dated Mar. 2, 2023.
Search Report issued in Chinese Application No. 201980092527.2, dated Mar. 1, 2023.
Croft, M., "The evolving crosstalk between co-stimulatory and co-inhibitory receptors: HVEM-BTLA", Trends in Immunology, 26(6): 292-294 (2005).
Extended European Search Report issued in EP Application No. 19906351.2, dated Jan. 16, 2023.
Markert et al., "Conditionally replicating herpes simplex virus mutant, G207 for the treatment of malignant glioma, results of a phase I trial", Gene Therapy, 7(10): 867-874 (2000).
Park et al., "Expression of anti-HVEM single-chain antibody on tumor cells induces tumor-specific immunity with long-term memory", Cancer Immunology Immunotherapy, 61(2): 203-214 (2011).

(Continued)

*Primary Examiner* — Emily A Cordas
(74) *Attorney, Agent, or Firm* — Knobbe, Martens, Olson & Bear, LLP

(57) ABSTRACT

A novel agent is for treating or preventing a glioma. A marker for malignancy of a brain tumor and a prognostic marker for a brain tumor can be used in a method for determining malignancy of a brain tumor and a method for determining a prognosis for a brain tumor patient. The agent for treating or preventing a glioma can include an HVEM inhibitor as an active ingredient. The marker for malignancy of a brain tumor and the prognostic marker for a brain tumor can each include an HVEM protein or an HVEM gene. The method for determining malignancy of a brain tumor and the method for determining a prognosis for a brain tumor patient can each include measuring an HVEM expression amount in a biological sample of a subject.

7 Claims, 25 Drawing Sheets

Specification includes a Sequence Listing.

(56) References Cited

OTHER PUBLICATIONS

Office Action issued in Chinese Application No. 201980092527.2, dated Aug. 26, 2022.
Search Report issued in Chinese Application No. 201980092527.2, date Aug. 22, 2022.

a b a b d a a b b c

GL261-Red Fluc (25 days post-injection)

Isotype control IgG                Anti-mouse
                                   HVEM IgG Mouse brain tissue hematoxylin/eosin staining f

FR4 CDR3 FR3 CDR2 FR2 CDR1 FR1

VHH#1
VHH#2
VHH#3
VHH#4
VHH#5
VHH#6
VHH#7

FIGURE 13

SEQUENCE LISTING

<160> NUMBER OF SEQ ID NOS: 84

<210> SEQ ID NO 1
<211> LENGTH: 19
<212> TYPE: DNA
<213> ORGANISM: Homo sapiens

<400> SEQUENCE: 1
gaaggtgaag gtcggagtc                                                    19

<210> SEQ ID NO 2
<211> LENGTH: 20
<212> TYPE: DNA
<213> ORGANISM: Homo sapiens

<400> SEQUENCE: 2
gaagatggtg atgggatttc                                                   20

<210> SEQ ID NO 3
<211> LENGTH: 20
<212> TYPE: DNA
<213> ORGANISM: Homo sapiens

<400> SEQUENCE: 3
gtgtctgcag tgccaaatgt                                                   20

<210> SEQ ID NO 4
<211> LENGTH: 18
<212> TYPE: DNA
<213> ORGANISM: Homo sapiens

<400> SEQUENCE: 4
ccacacacgg cgttctct                                                     18

```
<210> SEQ ID NO 5
<211> LENGTH: 20
<212> TYPE: RNA
<213> ORGANISM: Artificial Sequence
<220> FEATURE:
<223> OTHER INFORMATION: scramble sequence

<400> SEQUENCE: 5
gugguuuaca ugucgacuaa                                            20

<210> SEQ ID NO 6
<211> LENGTH: 20
<212> TYPE: RNA
<213> ORGANISM: Artificial Sequence
<220> FEATURE:
<223> OTHER INFORMATION: scramble sequence

<400> SEQUENCE: 6
augguuuaca uguuguguga                                            20

<210> SEQ ID NO 7
<211> LENGTH: 21
<212> TYPE: RNA
<213> ORGANISM: Homo sapiens

<400> SEQUENCE: 7
gugcagucca gguuaucgug u                                          21

<210> SEQ ID NO 8
<211> LENGTH: 21
<212> TYPE: RNA
<213> ORGANISM: Homo sapiens

<400> SEQUENCE: 8
gagcugacgg gcacagugug u                                          21

<210> SEQ ID NO 9
<211> LENGTH: 21
<212> TYPE: DNA
<213> ORGANISM: Mus musculus

<400> SEQUENCE: 9
tgcagtggca aagtggagat t                                          21

<210> SEQ ID NO 10
<211> LENGTH: 18
<212> TYPE: DNA
<213> ORGANISM: Mus musculus

<400> SEQUENCE: 10
tgccgttgaa tttgccgt                                              18

<210> SEQ ID NO 11
<211> LENGTH: 20
<212> TYPE: DNA
<213> ORGANISM: Mus musculus

<400> SEQUENCE: 11
aatggaacct ctcccaggat                                            20

<210> SEQ ID NO 12
<211> LENGTH: 19
<212> TYPE: DNA
<213> ORGANISM: Mus musculus
```

<400> SEQUENCE: 12
aggaagacac aaggcacca                                                          19

<210> SEQ ID NO 13
<211> LENGTH: 21
<212> TYPE: RNA
<213> ORGANISM: Mus musculus

<400> SEQUENCE: 13
gcaacccagg uuaccaugug a                                                       21

<210> SEQ ID NO 14
<211> LENGTH: 21
<212> TYPE: RNA
<213> ORGANISM: Mus musculus

<400> SEQUENCE: 14
gugagcauac aggcacagug u                                                       21

<210> SEQ ID NO 15
<211> LENGTH: 21
<212> TYPE: RNA
<213> ORGANISM: Homo sapiens

<400> SEQUENCE: 15
gagacucuau uccgauguau a                                                       21

<210> SEQ ID NO 16
<211> LENGTH: 21
<212> TYPE: RNA
<213> ORGANISM: Homo sapiens

<400> SEQUENCE: 16
ggcaagggcg aaacuuaacc u                                                       21

<210> SEQ ID NO 17
<211> LENGTH: 20
<212> TYPE: DNA
<213> ORGANISM: Homo sapiens

<400> SEQUENCE: 17
tatagcgcag gtgtcttcca                                                         20

<210> SEQ ID NO 18
<211> LENGTH: 21
<212> TYPE: DNA
<213> ORGANISM: Homo sapiens

<400> SEQUENCE: 18
acagtttcac aaaccccagg a                                                       21

<210> SEQ ID NO 19
<211> LENGTH: 23
<212> TYPE: DNA
<213> ORGANISM: Artificial Sequence
<220> FEATURE:
<223> OTHER INFORMATION: Target sequence of control gRNA
<220> FEATURE:
<221> NAME/KEY: misc_feature
<222> LOCATION: (21)..(21)
<223> OTHER INFORMATION: n is a, c, g, or t

<400> SEQUENCE: 19

-continued

```
gtattactga tattggtggg ngg                                           23

<210> SEQ ID NO 20
<211> LENGTH: 23
<212> TYPE: DNA
<213> ORGANISM: Homo sapiens

<400> SEQUENCE: 20
agcagttccg gctcgcgcgc agg                                           23

<210> SEQ ID NO 21
<211> LENGTH: 23
<212> TYPE: DNA
<213> ORGANISM: Homo sapiens

<400> SEQUENCE: 21
ccctccggac gtcaccacgg tgg                                           23

<210> SEQ ID NO 22
<211> LENGTH: 23
<212> TYPE: DNA
<213> ORGANISM: Mus musculus

<400> SEQUENCE: 22
tgcgctgcag caagttcaaa agg                                           23

<210> SEQ ID NO 23
<211> LENGTH: 23
<212> TYPE: DNA
<213> ORGANISM: Mus musculus

<400> SEQUENCE: 23
gcggagtctg tgatccaggt agg                                           23

<210> SEQ ID NO 24
<211> LENGTH: 98
<212> TYPE: RNA
<213> ORGANISM: Artificial Sequence
<220> FEATURE:
<223> OTHER INFORMATION: Control gRNA

<400> SEQUENCE: 24
gguauuacug auauuggugg gguuuuagag cuagaaauag caaguuaaaa uaaggcuagu   60
ccguuaucaa cuugaaaaag uggcaccgag ucggugcu                          98

<210> SEQ ID NO 25
<211> LENGTH: 98
<212> TYPE: RNA
<213> ORGANISM: Homo sapiens

<400> SEQUENCE: 25
gagcaguucc ggcucgcgcg cguuuuagag cuagaaauag caaguuaaaa uaaggcuagu   60
ccguuaucaa cuugaaaaag uggcaccgag ucggugcu                          98

<210> SEQ ID NO 26
<211> LENGTH: 98
<212> TYPE: RNA
<213> ORGANISM: Homo sapiens

<400> SEQUENCE: 26
gcccuccgga cgucaccacg gguuuuagag cuagaaauag caaguuaaaa uaaggcuagu   60
ccguuaucaa cuugaaaaag uggcaccgag ucggugcu                          98
```

```
<210> SEQ ID NO 27
<211> LENGTH: 98
<212> TYPE: RNA
<213> ORGANISM: Mus musculus

<400> SEQUENCE: 27
gugcgcugca gcaaguucaa aguuuuagag cuagaaauag caaguuaaaa uaaggcuagu      60
ccguuaucaa cuugaaaaag uggcaccgag ucggugcu                              98

<210> SEQ ID NO 28
<211> LENGTH: 98
<212> TYPE: RNA
<213> ORGANISM: Mus musculus

<400> SEQUENCE: 28
ggcggagucu gugauccagg uguuuuagag cuagaaauag caaguuaaaa uaaggcuagu      60
ccguuaucaa cuugaaaaag uggcaccgag ucggugcu                              98

<210> SEQ ID NO 29
<211> LENGTH: 115
<212> TYPE: PRT
<213> ORGANISM: Vicugna pacos

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr His
            20                  25                  30

Ala Met Ser Trp Tyr Arg Gln Ala Pro Gly Lys Glu Arg Glu Leu Val
        35                  40                  45

Ala His Ile Ser Ser Thr Gly Gly Ser Thr Asn Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Arg Cys
                85                  90                  95

Asn Ala Arg Asp Trp Tyr Glu Tyr Trp Gly Arg Gly Thr Gln Val Thr
            100                 105                 110

Val Ser Ser
        115

<210> SEQ ID NO 30
<211> LENGTH: 117
<212> TYPE: PRT
<213> ORGANISM: Vicugna pacos

<400> SEQUENCE: 30

Gln Val Gln Leu Val Glu Ser Gly Gly Gly Leu Val Gln Pro Gly Gly
1               5                   10                  15

Ser Leu Arg Leu Ser Cys Val Ala Ser Gly Arg Leu Phe Asp Thr Tyr
            20                  25                  30

Thr Met Ala Trp Tyr Arg Leu Pro Pro Gly Lys Gln Arg Glu Leu Val
        35                  40                  45

Ala Asp Ile Ser Arg Thr Gly Phe Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80
```

-continued

Gln Met Asn Ser Leu Lys Pro Asp Asp Thr Ala His Tyr Arg Cys Lys
            85              90              95

Val Arg Glu Pro Ala Thr Met Tyr Glu Tyr Trp Gly Gln Gly Thr Gln
            100             105             110

Val Thr Val Ser Ser
        115

<210> SEQ ID NO 31
<211> LENGTH: 115
<212> TYPE: PRT
<213> ORGANISM: Vicugna pacos

<400> SEQUENCE: 31

Gln Val Gln Leu Val Glu Ser Gly Gly Gly Ser Val Gln Pro Gly Gly
1               5               10              15

Ser Leu Arg Leu Ser Cys Ala Ala Ser Gly Ser Ile Gly Ser Ile His
            20              25              30

Arg Trp Asp Trp Tyr Arg Leu Cys Pro Gly Lys Gln Arg Glu Trp Val
            35              40              45

Ala Thr Leu Asn Ser Glu Gly Gly Pro Thr Tyr Ala Asp Ser Val Glu
        50              55              60

Gly Arg Phe Thr Ile Ser Arg Asp Asn Ala Lys Asn Met Val Tyr Leu
65              70              75              80

Gln Met Asn Ser Leu Lys Pro Glu Asp Thr Ala Val Tyr Arg Cys Ser
            85              90              95

Ala Arg Thr Val Pro Phe Glu Tyr Trp Gly Arg Gly Thr Gln Val Thr
            100             105             110

Val Ser Ser
        115

<210> SEQ ID NO 32
<211> LENGTH: 118
<212> TYPE: PRT
<213> ORGANISM: Vicugna pacos

<400> SEQUENCE: 32

Gln Val Gln Leu Val Glu Ser Gly Gly Gly Leu Val Gln Pro Gly Gly
1               5               10              15

Ser Leu Arg Leu Ser Cys Ala Ala Ala Glu Ser Met Leu Ser Pro Tyr
            20              25              30

Ser Met Gly Trp Tyr Arg Leu Pro Pro Gly Lys Gln Arg Glu Leu Val
            35              40              45

Ala Ser Leu Gly Ser Gly Gly Arg Thr Thr Tyr Ala Asp Ser Val Lys
        50              55              60

Gly Arg Phe Thr Ile Ser Arg Asp Asn Ala Lys Asn Thr Ala Tyr Leu
65              70              75              80

Gln Met Asn Ser Leu Lys Pro Glu Asp Thr Ala Val Tyr Arg Cys Asn
            85              90              95

Ile Arg Glu Leu Leu Gly Arg Arg Tyr Glu Tyr Trp Ser Gln Gly Thr
            100             105             110

Gln Val Thr Val Ser Ser
        115

<210> SEQ ID NO 33
<211> LENGTH: 119
<212> TYPE: PRT
<213> ORGANISM: Vicugna pacos

```
<400> SEQUENCE: 33

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

His Met Thr Trp Val Arg Gln Ala Pro Gly Lys Gly Leu Glu Trp Val
        35                  40                  45

Ser Leu Ile Asn Ser Ser Gly Arg Thr Ala Tyr Val Asp Ser Val Ala
        50                  55                  60

Gly Arg Phe Thr Ile Ser Arg Asp Asn Ala Lys Asn Thr Leu Tyr Leu
65                  70                  75                  80

Gln Met Thr Asn Leu Lys Pro Glu Asp Thr Ala Val Tyr Tyr Cys Ser
                85                  90                  95

Lys Gly Gly Trp Asp Gly Leu Pro Ser Ser Ser Ile Arg Gly Gln Gly
            100                 105                 110

Thr Gln Val Thr Val Ser Ser
        115

<210> SEQ ID NO 34
<211> LENGTH: 112
<212> TYPE: PRT
<213> ORGANISM: Vicugna pacos

<400> SEQUENCE: 34

Gln Val Gln Leu Val Glu Ser Gly Gly Gly Leu Val Pro Ile Gly Gly
1               5                   10                  15

Ser Leu Arg Leu Ser Cys Ala Val Ser Gly Leu Ala Phe Asp Arg Tyr
            20                  25                  30

Thr Phe Asn Trp Tyr Arg Gln Ala Pro Gly Lys Gly Arg Glu Trp Val
        35                  40                  45

Ala Ser Ile Asp Ser Thr Ser Ala Val Ile Asp Tyr Glu Asp Thr Val
        50                  55                  60

Lys Gly Arg Phe Thr Ile Ser Arg Asp Asn Thr Lys Asn Thr Val Tyr
65                  70                  75                  80

Leu Gln Met Asn Ser Leu Lys Pro Glu Asp Thr Ala Val Tyr Phe Cys
                85                  90                  95

Gly Arg Gly Gly Tyr Tyr Gly Gln Gly Thr Gln Val Thr Val Ser Thr
            100                 105                 110

<210> SEQ ID NO 35
<211> LENGTH: 117
<212> TYPE: PRT
<213> ORGANISM: Vicugna pacos

<400> SEQUENCE: 35

Gln Val Gln Leu Val Glu Ser Gly Gly Gly Leu Val Gln Pro Gly Gly
1               5                   10                  15

Ser Leu Lys Leu Ser Cys Val Ala Ser Gly Phe Thr Asp Lys Pro Thr
            20                  25                  30

Tyr Trp Ser Trp Tyr Arg Gln Pro Pro Gly Lys Asp Arg Glu Leu Val
        35                  40                  45

Ala Arg Met His Thr Gly Gly Leu Gly Thr Ala Tyr Pro Asp Ser Val
        50                  55                  60

Ala Gly Arg Phe Thr Ile Ser Thr Val Asn Asp Lys Asn Thr Val Tyr
65                  70                  75                  80
```

```
Leu Gln Met Asn Ser Leu Lys Pro Glu Asp Thr Ala Val Tyr Tyr Cys
                85              90                  95

Asn Ala Glu Ile Ser Gly Gly Pro Asp Tyr Trp Gly Gln Gly Thr Gln
            100             105             110

Val Thr Val Ser Ser
        115

<210> SEQ ID NO 36
<211> LENGTH: 7
<212> TYPE: PRT
<213> ORGANISM: Vicugna pacos

<400> SEQUENCE: 36

Phe Ser Thr His Ala Met Ser
1               5

<210> SEQ ID NO 37
<211> LENGTH: 8
<212> TYPE: PRT
<213> ORGANISM: Vicugna pacos

<400> SEQUENCE: 37

His Ile Ser Ser Thr Gly Gly Ser
1               5

<210> SEQ ID NO 38
<211> LENGTH: 11
<212> TYPE: PRT
<213> ORGANISM: Vicugna pacos

<400> SEQUENCE: 38

Cys Asn Ala Arg Asp Trp Tyr Glu Tyr Trp Gly
1               5               10

<210> SEQ ID NO 39
<211> LENGTH: 9
<212> TYPE: PRT
<213> ORGANISM: Vicugna pacos

<400> SEQUENCE: 39

Arg Leu Phe Asp Thr Tyr Thr Met Ala
1               5

<210> SEQ ID NO 40
<211> LENGTH: 7
<212> TYPE: PRT
<213> ORGANISM: Vicugna pacos

<400> SEQUENCE: 40

Asp Ile Ser Arg Thr Gly Phe
1               5

<210> SEQ ID NO 41
<211> LENGTH: 13
<212> TYPE: PRT
<213> ORGANISM: Vicugna pacos

<400> SEQUENCE: 41

Cys Lys Val Arg Glu Pro Ala Thr Met Tyr Glu Tyr Trp
1               5               10

<210> SEQ ID NO 42
<211> LENGTH: 9
<212> TYPE: PRT
```

```
<213> ORGANISM: Vicugna pacos

<400> SEQUENCE: 42

Ser Ile Gly Ser Ile His Arg Trp Asp
1               5

<210> SEQ ID NO 43
<211> LENGTH: 7
<212> TYPE: PRT
<213> ORGANISM: Vicugna pacos

<400> SEQUENCE: 43

Thr Leu Asn Ser Glu Gly Gly
1               5

<210> SEQ ID NO 44
<211> LENGTH: 11
<212> TYPE: PRT
<213> ORGANISM: Vicugna pacos

<400> SEQUENCE: 44

Cys Ser Ala Arg Thr Val Pro Phe Glu Tyr Trp
1               5                   10

<210> SEQ ID NO 45
<211> LENGTH: 9
<212> TYPE: PRT
<213> ORGANISM: Vicugna pacos

<400> SEQUENCE: 45

Ser Met Leu Ser Pro Tyr Ser Met Gly
1               5

<210> SEQ ID NO 46
<211> LENGTH: 7
<212> TYPE: PRT
<213> ORGANISM: Vicugna pacos

<400> SEQUENCE: 46

Ser Leu Gly Ser Gly Gly Arg
1               5

<210> SEQ ID NO 47
<211> LENGTH: 14
<212> TYPE: PRT
<213> ORGANISM: Vicugna pacos

<400> SEQUENCE: 47

Cys Asn Ile Arg Glu Leu Leu Gly Arg Arg Tyr Glu Tyr Trp
1               5                   10

<210> SEQ ID NO 48
<211> LENGTH: 9
<212> TYPE: PRT
<213> ORGANISM: Vicugna pacos

<400> SEQUENCE: 48

Phe Thr Phe Ser Ser Ser His Met Thr
1               5

<210> SEQ ID NO 49
<211> LENGTH: 7
<212> TYPE: PRT
<213> ORGANISM: Vicugna pacos
```

-continued

<400> SEQUENCE: 49

Leu Ile Asn Ser Ser Gly Arg
1               5

<210> SEQ ID NO 50
<211> LENGTH: 15
<212> TYPE: PRT
<213> ORGANISM: Vicugna pacos

<400> SEQUENCE: 50

Cys Ser Lys Gly Gly Trp Asp Gly Leu Pro Ser Ser Ser Ile Arg
1               5                   10              15

<210> SEQ ID NO 51
<211> LENGTH: 9
<212> TYPE: PRT
<213> ORGANISM: Vicugna pacos

<400> SEQUENCE: 51

Leu Ala Phe Asp Arg Tyr Thr Phe Asn
1               5

<210> SEQ ID NO 52
<211> LENGTH: 8
<212> TYPE: PRT
<213> ORGANISM: Vicugna pacos

<400> SEQUENCE: 52

Ser Ile Asp Ser Thr Ser Ala Val
1               5

<210> SEQ ID NO 53
<211> LENGTH: 7
<212> TYPE: PRT
<213> ORGANISM: Vicugna pacos

<400> SEQUENCE: 53

Cys Gly Arg Gly Gly Tyr Tyr
1               5

<210> SEQ ID NO 54
<211> LENGTH: 9
<212> TYPE: PRT
<213> ORGANISM: Vicugna pacos

<400> SEQUENCE: 54

Phe Thr Asp Lys Pro Thr Tyr Trp Ser
1               5

<210> SEQ ID NO 55
<211> LENGTH: 7
<212> TYPE: PRT
<213> ORGANISM: Vicugna pacos

<400> SEQUENCE: 55

Met His Thr Gly Gly Leu Gly
1               5

<210> SEQ ID NO 56
<211> LENGTH: 12
<212> TYPE: PRT
<213> ORGANISM: Vicugna pacos

<400> SEQUENCE: 56

```
Cys Asn Ala Glu Ile Ser Gly Gly Pro Asp Tyr Trp
1               5                   10

<210> SEQ ID NO 57
<211> LENGTH: 28
<212> TYPE: PRT
<213> ORGANISM: Vicugna pacos

<400> SEQUENCE: 57

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr
            20                  25

<210> SEQ ID NO 58
<211> LENGTH: 14
<212> TYPE: PRT
<213> ORGANISM: Vicugna pacos

<400> SEQUENCE: 58

Trp Tyr Arg Gln Ala Pro Gly Lys Glu Arg Glu Leu Val Ala
1               5                   10

<210> SEQ ID NO 59
<211> LENGTH: 38
<212> TYPE: PRT
<213> ORGANISM: Vicugna pacos

<400> SEQUENCE: 59

Thr Asn Tyr Ala Asp Ser Val Lys Gly Arg Phe Thr Ile Ser Arg Asp
1               5                   10                  15

Asn Ala Lys Asn Thr Val Tyr Leu Gln Met Asn Ser Leu Lys Pro Glu
            20                  25                  30

Asp Thr Ala Val Tyr Arg
            35

<210> SEQ ID NO 60
<211> LENGTH: 9
<212> TYPE: PRT
<213> ORGANISM: Vicugna pacos

<400> SEQUENCE: 60

Arg Gly Thr Gln Val Thr Val Ser Ser
1               5

<210> SEQ ID NO 61
<211> LENGTH: 26
<212> TYPE: PRT
<213> ORGANISM: Vicugna pacos

<400> SEQUENCE: 61

Gln Val Gln Leu Val Glu Ser Gly Gly Gly Leu Val Gln Pro Gly Gly
1               5                   10                  15

Ser Leu Arg Leu Ser Cys Val Ala Ser Gly
            20                  25

<210> SEQ ID NO 62
<211> LENGTH: 14
<212> TYPE: PRT
<213> ORGANISM: Vicugna pacos

<400> SEQUENCE: 62

Trp Tyr Arg Leu Pro Pro Gly Lys Gln Arg Glu Leu Val Ala
```

-continued

```
1               5                  10
```

```
<210> SEQ ID NO 63
<211> LENGTH: 38
<212> TYPE: PRT
<213> ORGANISM: Vicugna pacos

<400> SEQUENCE: 63

Thr Asn Tyr Ala Asp Ser Val Lys Gly Arg Phe Thr Ile Ser Arg Asp
1               5                  10                  15

Asn Ala Lys Asn Thr Val Tyr Leu Gln Met Asn Ser Leu Lys Pro Asp
            20                  25                  30

Asp Thr Ala His Tyr Arg
        35

<210> SEQ ID NO 64
<211> LENGTH: 10
<212> TYPE: PRT
<213> ORGANISM: Vicugna pacos

<400> SEQUENCE: 64

Gly Gln Gly Thr Gln Val Thr Val Ser Ser
1               5                  10

<210> SEQ ID NO 65
<211> LENGTH: 26
<212> TYPE: PRT
<213> ORGANISM: Vicugna pacos

<400> SEQUENCE: 65

Gln Val Gln Leu Val Glu Ser Gly Gly Gly Ser Val Gln Pro Gly Gly
1               5                  10                  15

Ser Leu Arg Leu Ser Cys Ala Ala Ser Gly
            20                  25

<210> SEQ ID NO 66
<211> LENGTH: 14
<212> TYPE: PRT
<213> ORGANISM: Vicugna pacos

<400> SEQUENCE: 66

Trp Tyr Arg Leu Cys Pro Gly Lys Gln Arg Glu Trp Val Ala
1               5                  10

<210> SEQ ID NO 67
<211> LENGTH: 38
<212> TYPE: PRT
<213> ORGANISM: Vicugna pacos

<400> SEQUENCE: 67

Pro Thr Tyr Ala Asp Ser Val Glu Gly Arg Phe Thr Ile Ser Arg Asp
1               5                  10                  15

Asn Ala Lys Asn Met Val Tyr Leu Gln Met Asn Ser Leu Lys Pro Glu
            20                  25                  30

Asp Thr Ala Val Tyr Arg
        35

<210> SEQ ID NO 68
<211> LENGTH: 10
<212> TYPE: PRT
<213> ORGANISM: Vicugna pacos

<400> SEQUENCE: 68
```

-continued

```
Gly Arg Gly Thr Gln Val Thr Val Ser Ser
1               5                   10

<210> SEQ ID NO 69
<211> LENGTH: 26
<212> TYPE: PRT
<213> ORGANISM: Vicugna pacos

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ala Glu
            20                  25

<210> SEQ ID NO 70
<211> LENGTH: 14
<212> TYPE: PRT
<213> ORGANISM: Vicugna pacos

<400> SEQUENCE: 70

Trp Tyr Arg Leu Pro Pro Gly Lys Gln Arg Glu Leu Val Ala
1               5                   10

<210> SEQ ID NO 71
<211> LENGTH: 38
<212> TYPE: PRT
<213> ORGANISM: Vicugna pacos

<400> SEQUENCE: 71

Thr Thr Tyr Ala Asp Ser Val Lys Gly Arg Phe Thr Ile Ser Arg Asp
1               5                   10                  15

Asn Ala Lys Asn Thr Ala Tyr Leu Gln Met Asn Ser Leu Lys Pro Glu
            20                  25                  30

Asp Thr Ala Val Tyr Arg
            35

<210> SEQ ID NO 72
<211> LENGTH: 10
<212> TYPE: PRT
<213> ORGANISM: Vicugna pacos

<400> SEQUENCE: 72

Ser Gln Gly Thr Gln Val Thr Val Ser Ser
1               5                   10

<210> SEQ ID NO 73
<211> LENGTH: 26
<212> TYPE: PRT
<213> ORGANISM: Vicugna pacos

<400> SEQUENCE: 73

Gln Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 74
<211> LENGTH: 14
<212> TYPE: PRT
<213> ORGANISM: Vicugna pacos

<400> SEQUENCE: 74
```

```
Trp Val Arg Gln Ala Pro Gly Lys Gly Leu Glu Trp Val Ser
1               5                   10

<210> SEQ ID NO 75
<211> LENGTH: 38
<212> TYPE: PRT
<213> ORGANISM: Vicugna pacos

<400> SEQUENCE: 75

Thr Ala Tyr Val Asp Ser Val Ala Gly Arg Phe Thr Ile Ser Arg Asp
1               5                   10                  15

Asn Ala Lys Asn Thr Leu Tyr Leu Gln Met Thr Asn Leu Lys Pro Glu
            20                  25                  30

Asp Thr Ala Val Tyr Tyr
        35

<210> SEQ ID NO 76
<211> LENGTH: 10
<212> TYPE: PRT
<213> ORGANISM: Vicugna pacos

<400> SEQUENCE: 76

Gly Gln Gly Thr Gln Val Thr Val Ser Ser
1               5                   10

<210> SEQ ID NO 77
<211> LENGTH: 26
<212> TYPE: PRT
<213> ORGANISM: Vicugna pacos

<400> SEQUENCE: 77

Gln Val Gln Leu Val Glu Ser Gly Gly Gly Leu Val Pro Ile Gly Gly
1               5                   10                  15

Ser Leu Arg Leu Ser Cys Ala Val Ser Gly
            20                  25

<210> SEQ ID NO 78
<211> LENGTH: 14
<212> TYPE: PRT
<213> ORGANISM: Vicugna pacos

<400> SEQUENCE: 78

Trp Tyr Arg Gln Ala Pro Gly Lys Gly Arg Glu Trp Val Ala
1               5                   10

<210> SEQ ID NO 79
<211> LENGTH: 38
<212> TYPE: PRT
<213> ORGANISM: Vicugna pacos

<400> SEQUENCE: 79

Ile Asp Tyr Glu Asp Thr Val Lys Gly Arg Phe Thr Ile Ser Arg Asp
1               5                   10                  15

Asn Thr Lys Asn Thr Val Tyr Leu Gln Met Asn Ser Leu Lys Pro Glu
            20                  25                  30

Asp Thr Ala Val Tyr Phe
        35

<210> SEQ ID NO 80
<211> LENGTH: 10
<212> TYPE: PRT
<213> ORGANISM: Vicugna pacos
```

-continued

```
<400> SEQUENCE: 80

Gly Gln Gly Thr Gln Val Thr Val Ser Thr
1               5                   10

<210> SEQ ID NO 81
<211> LENGTH: 26
<212> TYPE: PRT
<213> ORGANISM: Vicugna pacos

<400> SEQUENCE: 81

Gln Val Gln Leu Val Glu Ser Gly Gly Gly Leu Val Gln Pro Gly Gly
1               5                   10                  15

Ser Leu Lys Leu Ser Cys Val Ala Ser Gly
            20                  25

<210> SEQ ID NO 82
<211> LENGTH: 15
<212> TYPE: PRT
<213> ORGANISM: Vicugna pacos

<400> SEQUENCE: 82

Trp Tyr Arg Gln Pro Pro Gly Lys Asp Arg Glu Leu Val Ala Arg
1               5                   10                  15

<210> SEQ ID NO 83
<211> LENGTH: 38
<212> TYPE: PRT
<213> ORGANISM: Vicugna pacos

<400> SEQUENCE: 83

Thr Ala Tyr Pro Asp Ser Val Ala Gly Arg Phe Thr Ile Ser Thr Val
1               5                   10                  15

Asn Asp Lys Asn Thr Val Tyr Leu Gln Met Asn Ser Leu Lys Pro Glu
            20                  25                  30

Asp Thr Ala Val Tyr Tyr
        35

<210> SEQ ID NO 84
<211> LENGTH: 10
<212> TYPE: PRT
<213> ORGANISM: Vicugna pacos

<400> SEQUENCE: 84

Gly Gln Gly Thr Gln Val Thr Val Ser Ser
1               5                   10
```

THERAPEUTIC AND PROPHYLACTIC AGENT FOR GLIOMA, BRAIN TUMOR MALIGNANCY MARKER, BRAIN TUMOR PROGNOSTIC MARKER, METHOD FOR DETERMINING MALIGNANCY AND PROGNOSIS OF BRAIN TUMOR AND ANTIBODY INHIBITING TUMOR PROLIFERATION

CROSS-REFERENCE TO RELATED APPLICATION

The present application enjoys the benefit of priority from the prior Japanese Patent Application No. 2018-248465 (filed on: Dec. 28, 2018), the entire disclosure of which is incorporated herein by reference.

TECHNICAL FIELD

The present invention relates to an agent for treating or preventing a glioma. The present invention also relates to a marker for malignancy of a brain tumor and a prognostic marker for a brain tumor, as well as a method for determining malignancy of a brain tumor and a method for determining a prognosis of a brain tumor. The present invention also relates to an antibody suppressing tumor growth.

BACKGROUND ART

The frequency of development of primary brain tumors in Japan is estimated to be approximately 20,000 persons per year (the prevalence in 2010 was 130.8 persons per 100,000 persons), and glioma, meningioma, pituitary adenoma, schwannoma and craniopharyngioma are known as so-called five major brain tumors. Brain tumors are generally treated by surgical tumor excision, but, in the case of malignant brain tumors, multidisciplinary treatment in which an anticancer drug, radiation therapy and the like are further combined with such surgical tumor excision is performed. The therapeutic effect depends on how much the tumor could be excised in the first surgery, and, in the case of malignant tumors, it has been reported that, unless 95 to 98% or more of the entire tumor is excised, the life prognosis is not so much different from that when only half of the tumor is excised. In addition, among brain tumors, malignant brain tumors are said to develop into more highly malignant brain tumors, with a high probability.

Glioblastoma multiforme (hereinafter sometimes referred to as "GBM") is the most common and most malignant form of malignant brain tumor in adults. Despite advances in surgery, radiation therapy and chemotherapy, glioblastoma patients still have a poor prognosis with a median survival time of less than 15 months. Glioblastoma is classified into proneural, neural, classical and mesenchymal subtypes based on the genomic aberrations identified by The Cancer Genome Atlas (TCGA) dataset. The highly proliferating property of glioblastoma cells is due to changes in several signaling pathways including oncogenes and tumor suppressor genes.

Bone morphogenetic proteins (hereinafter referred to as "BMPs") are members of the TGF-β superfamily, and members of the BMP subfamily including BMP-2, BMP-4 and BMP-7 have been reported to induce differentiation, cell cycle arrest and apoptosis of glioblastoma cells. The BMP target genes, which have been identified in glioblastoma so far, contain a large amount of intracellular signal molecules (Non-Patent Document 1).

REFERENCE LIST

Non-Patent Documents

Non-Patent Document 1: Savary K et al., Oncogene, 32:5409-5420 (2013)

SUMMARY OF THE INVENTION

Under such technical background, the present inventors have found that BMP-4 induces growth arrest and differentiation of glioblastoma-initiating cells (GICs), and, additionally, that HVEM expression in specific glioblastoma cells is suppressed by BMP-4. The present inventors have also found that HVEM expression preferentially increases in glioblastoma multiforme among human adult brain tumors, and that HVEM is most highly expressed in the mesenchymal subtype among the four subtypes of GBM. The present inventors have also found that suppression of HVEM expression in mesenchymal subtype cell culture resulted in reduced cell proliferation and neurosphere formation, and that intracranial injection of mesenchymal subtype cells with suppressed HVEM expression into mice reduces tumorigenicity and prolongs the survive time of the mice. The present inventors have also found that overexpression of HVEM enhances proliferation of glioblastoma cells and neurosphere formation in cell culture, and that intracranial injection of the cells shortens the survival time of the mice. Further, the present inventors have found that intraperitoneal administration of an anti-mouse HVEM antibody to mice intracranially and orthotopically transplanted with HVEM-expressing murine glioma GL261 cells decreases tumorigenicity and prolongs the survival time of the mice. The present inventors have also found that, in GBM, expression of APRIL, which has not been reported as a ligand for HVEM, is high, while expression of known ligands for HVEM are low. The present inventors have also found that suppression of APRIL expression in mesenchymal subtype cell culture attenuates cell proliferation and neurosphere formation. The present inventors have also found that APRIL transduces signals to HVEM by co-culturing HVEM-expressing cells and APRIL-expressing cells. Further, the present inventors have found that an anti-human HVEM antibody prepared in an alpaca suppresses proliferation of mesenchymal subtype cells. The present invention is based on such findings.

An object of the present invention is to provide a novel agent for treating or preventing a glioma. Another object of the present invention is to provide a marker for malignancy of a brain tumor and a prognostic marker for a brain tumor. Still another object of the present invention is to provide a method for determining malignancy of a brain tumor and a method for determining a prognosis for a brain tumor patient. Still another object of the present invention is to provide a novel antibody suppressing tumor growth.

According to the present invention, the following inventions are provided.

[1] An agent for treating or preventing a glioma, comprising an HVEM inhibitor as an active ingredient.

[2] The agent according to [1], wherein the glioma is any one of oligodendroglioma, oligoastrocytoma, astrocytoma and glioblastoma multiforme.

[3] The agent according to [2], wherein the glioblastoma multiforme belongs to any of proneural subtype, neural subtype, classical subtype and mesenchymal subtype.

[4] The agent according to any one of [1] to [3], wherein the HVEM inhibitor is an antibody or nucleic acid against HVEM.

[5] The agent according to [4], wherein the antibody against HVEM is an antibody which inhibits binding between HVEM and a ligand.

[6] The agent according to any one of [1] to [5], wherein the glioma is HVEM expression-dependent glioma or HVEM ligand-dependent glioma.

[7] The agent according to [5] or [6], wherein the ligand is APRIL.

[8] The agent according to any one of [1] to [7], which is used to be administered to a subject whose HVEM expression amount exceeds an HVEM expression amount in a healthy subject or an HVEM expression amount in a normal tissue sample.

[9]A marker for malignancy of a brain tumor or a prognostic marker for a brain tumor, each consisting of an HVEM protein or an HVEM gene.

[10]A method for determining malignancy of a brain tumor, the method comprising the step of measuring an HVEM expression amount in a biological sample of a subject.

[11] The method according to [10], wherein it is indicated that the biological sample contains a highly malignant tumor cell population if the HVEM expression amount in the biological sample of the subject exceeds the HVEM expression amount in a biological sample of a healthy subject or in a normal tissue sample.

[12] The method according to [10], wherein it is indicated that the subject suffers from a highly malignant brain tumor if the HVEM expression amount in the biological sample of the subject exceeds the HVEM expression amount in a biological sample of a healthy subject or in a normal tissue sample.

[13]A method for determining a prognosis for a brain tumor patient, the method comprising the step of measuring an HVEM expression amount in a biological sample of a subject.

[14] The method according to [13], wherein it is indicated that the subject has a poor prognosis if the HVEM expression amount in the biological sample of the subject exceeds the HVEM expression amount in a biological sample of a healthy subject or in a normal tissue sample.

[15] An immunoglobulin single variable domain which binds to HVEM at an EC50 value of less than 80 nM, and suppresses tumor growth.

[16] The immunoglobulin single variable domain according to [15], which comprises complementarity determining regions 1 to 3 (CDR1, CDR2 and CDR3), wherein amino acid sequences of CDR1, CDR2 and CDR3 are the following (i), (ii), (iii), (iv), (v), (vi) or (vii):

(i) CDR1 comprising an amino acid sequence represented by SEQ ID NO: 36, CDR2 comprising an amino acid sequence represented by SEQ ID NO: 37, and CDR3 comprising an amino acid sequence represented by SEQ ID NO: 38;

(ii) CDR1 comprising an amino acid sequence represented by SEQ ID NO: 39, CDR2 comprising an amino acid sequence represented by SEQ ID NO: 40, and CDR3 comprising an amino acid sequence represented by SEQ ID NO: 41;

(iii) CDR1 comprising an amino acid sequence represented by SEQ ID NO: 42, CDR2 comprising an amino acid sequence represented by SEQ ID NO: 43, and CDR3 comprising an amino acid sequence represented by SEQ ID NO: 44;

(iv) CDR1 comprising an amino acid sequence represented by SEQ ID NO: 45, CDR2 comprising an amino acid sequence represented by SEQ ID NO: 46, and CDR3 comprising an amino acid sequence represented by SEQ ID NO: 47;

(v) CDR1 comprising an amino acid sequence represented by SEQ ID NO: 48, CDR2 comprising an amino acid sequence represented by SEQ ID NO: 49, and CDR3 comprising an amino acid sequence represented by SEQ ID NO: 50;

(vi) CDR1 comprising an amino acid sequence represented by SEQ ID NO: 51, CDR2 comprising an amino acid sequence represented by SEQ ID NO: 52, and CDR3 comprising an amino acid sequence represented by SEQ ID NO: 53; or (vii) CDR1 comprising an amino acid sequence represented by SEQ ID NO: 54, CDR2 comprising an amino acid sequence represented by SEQ ID NO: 55, and CDR3 comprising an amino acid sequence represented by SEQ ID NO: 56.

[17] The immunoglobulin single variable domain according to [16], which comprises framework regions (FR1, FR2, FR3 and FR4), wherein amino acid sequences of FR1, FR2, FR3 and FR4 are the following (viii), (ix), (x), (xi), (xii), (xiii) or (xiv):

(viii) FR1 comprising an amino acid sequence represented by SEQ ID NO: 57, FR2 comprising an amino acid sequence represented by SEQ ID NO: 58, FR3 comprising an amino acid sequence represented by SEQ ID NO: 59, and FR4 comprising an amino acid sequence represented by SEQ ID NO: 60;

(ix) FR1 comprising an amino acid sequence represented by SEQ ID NO: 61, FR2 comprising an amino acid sequence represented by SEQ ID NO: 62, FR3 comprising an amino acid sequence represented by SEQ ID NO: 63, and FR4 comprising an amino acid sequence represented by SEQ ID NO: 64;

(x) FR1 comprising an amino acid sequence represented by SEQ ID NO: 65, FR2 comprising an amino acid sequence represented by SEQ ID NO: 66, FR3 comprising an amino acid sequence represented by SEQ ID NO: 67, and FR4 comprising an amino acid sequence represented by SEQ ID NO: 68;

(xi) FR1 comprising an amino acid sequence represented by SEQ ID NO: 69, FR2 comprising an amino acid sequence represented by SEQ ID NO: 70, FR3 comprising an amino acid sequence represented by SEQ ID NO: 71, and FR4 comprising an amino acid sequence represented by SEQ ID NO: 72;

(xii) FR1 comprising an amino acid sequence represented by SEQ ID NO: 73, FR2 comprising an amino acid sequence represented by SEQ ID NO: 74, FR3 comprising an amino acid sequence represented by SEQ ID NO: 75, and FR4 comprising an amino acid sequence represented by SEQ ID NO: 76;

(xiii) FR1 comprising an amino acid sequence represented by SEQ ID NO: 77, FR2 comprising an amino acid sequence represented by SEQ ID NO: 78, FR3 comprising an amino acid sequence represented by SEQ ID NO: 79, and FR4 comprising an amino acid sequence represented by SEQ ID NO: 80; or (xiv) FR1 comprising an amino acid sequence represented by SEQ ID NO: 81, FR2 comprising an amino acid sequence represented by SEQ ID NO: 82, FR3 comprising an amino acid sequence represented by SEQ ID NO: 83, and FR4 comprising an amino acid sequence represented by SEQ ID NO: 84.

[18] The immunoglobulin single variable domain according to [15], which comprises the following polypeptide (xv), (xvi) or (xvii):

(xv) a polypeptide having an amino acid sequence of any of SEQ ID NOs: 29 to 35;

(xvi) a polypeptide comprising an amino acid sequence having at least 80% identity to the amino acid sequence of any of SEQ ID NOs: 29 to 35, and having HVEM binding ability and tumor growth suppression ability; or (xvii) a polypeptide comprising an amino acid sequence in which one or more amino acids is/are deleted, substituted, inserted and/or added in the amino acid sequence of any of SEQ ID NOs: 29 to 35, and having HVEM binding ability and tumor growth suppression ability.

[19] An antibody or an immunoglobulin single variable domain multimer, each comprising the immunoglobulin single variable domain according to any one of [15] to [18].

[20] A polynucleotide encoding the immunoglobulin single variable domain according to any one of [15] to [18] or the antibody or multimer according to [19].

[21] A pharmaceutical composition comprising the immunoglobulin single variable domain according to any one of [15] to [18] or the antibody or multimer according to [19].

[22] The pharmaceutical composition according to [21] which is for use in the treatment or prevention of a glioma.

[23] An agent for reducing the risk of developing a glioma and a composition for use in the reduction of the risk of developing a glioma, each comprising an HVEM inhibitor as an active ingredient.

[24] An agent for improving a prognosis in treatment of a brain tumor and a composition for use in the improvement of a prognosis in the treatment of a brain tumor, each comprising an HVEM inhibitor as an active ingredient.

[25] A method for treating or preventing a glioma, comprising the step of administering an effective amount of an HVEM inhibitor to a subject in need thereof.

[26] A method for treating a glioma, comprising the steps of: carrying out the method for determining malignancy of a brain tumor according to any one of [10] to [12]; and administering an effective amount of an anticancer agent (especially, an HVEM inhibitor) to a subject determined to suffer from, or to be highly likely to suffer from, a highly malignant brain tumor (or a subject determined to suffer from, or to be highly likely to suffer from, a glioma).

In the present specification, the agents according to the above [1], the above [23] and the above [24] are sometimes referred to as "the agents of the present invention," and the compositions according to the above [1], the above [23] and the above [24] are sometimes referred to as "the compositions of the present invention."

According to the present invention, there can be provided a novel agent for treating or preventing a glioma, which is considered as a disease that occurs relatively frequently among brain tumors and is difficult to cure, and means for determining malignancy of a brain tumor and a prognosis of a brain tumor patient. Among brain tumors, glioma (especially, glioblastoma multiforme) is one of malignant tumors having the highest malignancy and the poorest prognosis, and no sufficient therapeutic effect has been obtained by surgery, radiation therapy or chemotherapy. Therefore, the present invention is advantageous in that it can provide a novel therapeutic strategy for malignant brain tumors including gliomas.

BRIEF DESCRIPTION OF THE DRAWINGS

FIG. 5a is also a diagram showing that, in Example 5, silencing of HVEM attenuates the in vivo tumorigenic activity of the mesenchymal subtype cells. Images of the mesenchymal subtype cells expressing shRNAs and firefly luciferase in the mouse skull by an in vivo bioluminescence imaging system. The luminescence intensity of the tumor composed of firefly luciferase-expressing GBM cells orthotopically transplanted into the mouse head was observed 15 weeks after the transplantation. For U3054MG cells, four mice each were used in the experiment. A region shown in black in the mouse head is the tumor composed of the GBM cells, and a white region in the center thereof is a portion with a higher emission intensity (count per second; cps) (about 800 to 3,800 cps) than that of the peripheral part.

FIG. 13 is a diagram showing amino acid sequences of variable regions of alpaca-derived VHH antibodies using human HVEM protein as an antigen in Example 12. CDR represents a complementarity determining region, and FR represents a framework region.

DETAILED DESCRIPTION OF THE INVENTION

Agent for Treating or Preventing Glioma

Figure 1:
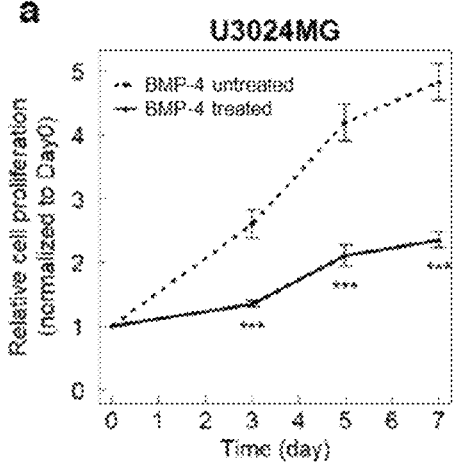
FIG. 1a is a diagram showing an inhibitory effect of BMP signaling on GBM cells in Example 1. Growth curves of GBM cells (U3024MG, U3031MG and U3054MG) were measured in the presence or absence of 30 ng/mL of recombinant human BMP-4. Data is indicated as mean±SD (n=3 biological replicates; P<0.01, *P<0.001; two-tailed unpaired Student's t-test for a cell proliferation assay).
FIG. 1b is a diagram showing the inhibitory effect of BMP signaling on the GBM cells in Example 1. Sphere formation of the GBM cells (U3024MG, U3031MG and U3054MG) were measured in the presence or absence of 30 ng/mL of recombinant human BMP-4. Data is indicated as mean±SD (n=3 biological replicates; P<0.01, *P<0.001; two-way analysis of variance for a sphere formation assay).
Figure 1:
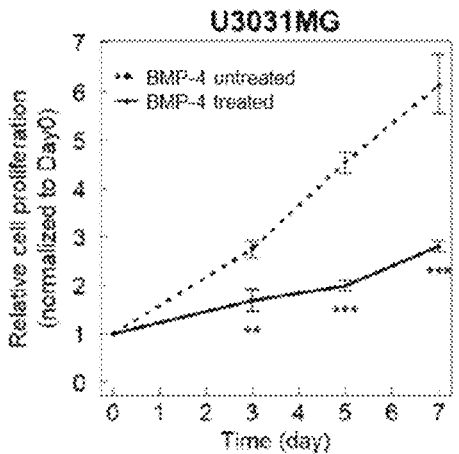
Figure 1:
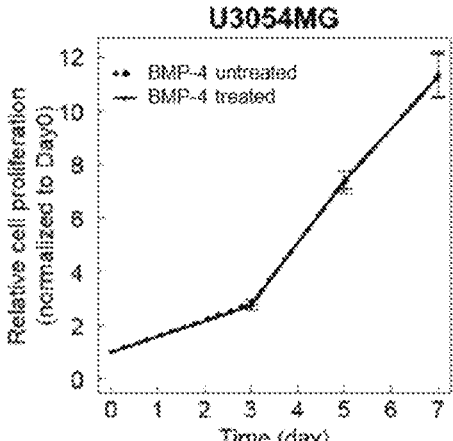
Figure 1:
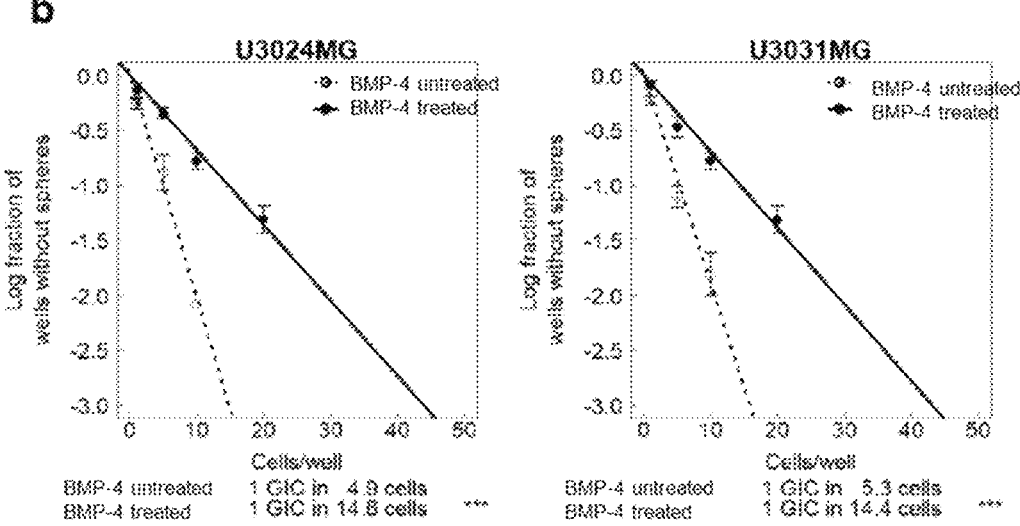
Figure 1:
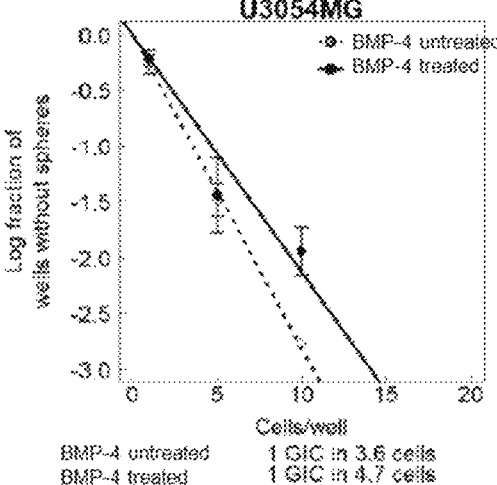

The agents and compositions of the present invention each comprise an HVEM inhibitor as an active ingredient. As used herein, the "HVEM" is an abbreviation for Herpes Virus entry mediator, and refers to a type I transmembrane protein belonging to the TNF/NGF receptor superfamily. HVEM is also referred to as TNFRSF14 (tumor necrosis factor (TNF) receptor superfamily member 14), CD270, LIGHTR or ATAR. That is, the "HVEM" in the present invention is synonymous with "HVEM/TNFRSF14."

HVEM is expressed on a variety of tissues and cells including T cells, B cells, natural killer cells, dendritic cells, hematopoietic cells and non-hematopoietic cells (parenchymal cells) (Pasero C et al., Curr Opin Pharmacol., 12: 478-485 (2012)). A plurality of ligands are known to bind to HVEM, including TNF-related cytokines such as LIGHT and LTα and non-TNF-related cytokines such as BTLA, CD160 and SALM5.

In the present invention, the human HVEM gene is based on the base sequence published in HGNC:11912, and the mouse HVEM gene is based on the base sequence published in MGI:2675303. Also, in the present invention, the human HVEM protein is based on the amino acid sequence published in GenBank Accession No. NP_003811.2, and the mouse HVEM protein is based on the amino acid sequence published in GenBank Accession No. NP_849262.1. Further, in the present invention, mRNA of human HVEM is based on GenBank Accession No. NM_003820.3, and mRNA of mouse HVEM is based on GenBank Accession No. NM_178931.2.

In the present invention, the HVEM inhibitor is used in the meaning including a substance which inhibits expression of HVEM and a substance which inhibits the function of HVEM. Examples of the substance which inhibits expression of HVEM include nucleic acids against HVEM (e.g., nucleic acids targeting HVEM such as antisense nucleic acids, siRNAs, shRNAs, microRNAs, gRNAs, and ribozymes). The substance which inhibits the function of HVEM is, for example, a substance which inhibits binding between HVEM and a ligand, in addition to a substance which interacts with HVEM to inhibit the function, and examples thereof include antibodies and aptamers.

APRIL is indicated as the ligand for HVEM. Since signal transduction from APRIL via HVEM was confirmed to promote formation of a tumor (especially, a highly malignant brain tumor such as glioma) as will be presented in the Examples below, a substance which inhibits binding between HVEM and APRIL can be used to efficiently suppress the formation of the tumor. The "APRIL," as used herein, is an abbreviation for "a proliferation-inducing ligand," and is also referred to as TNFSF13 (tumor necrosis factor (TNF) superfamily member 13). That is, the "APRIL" in the present invention is synonymous with "APRIL/TNFSF13."

Antisense nucleic acids are nucleic acids complementary to a target sequence. The antisense nucleic acid can suppress expression of the target gene, for example, through inhibition of transcription initiation by triple-strand formation, suppression of transcription by hybrid formation with a site where an open loop structure is locally formed by RNA polymerase, inhibition of transcription by hybrid formation with RNA which is being synthesized, suppression of splicing by hybrid formation at a junction point between an intron and an exon, suppression of splicing by hybrid formation with a spliceosome formation site, suppression of migration from the nucleus to the cytoplasm by hybrid formation with mRNA, suppression of splicing by hybrid formation with a capping site and a poly (A) addition site, inhibition of translation initiation by hybrid formation with a translation initiation factor binding site, suppression of translation by hybrid formation with a ribosome binding site near the initiation codon, inhibition of peptide chain elongation by hybrid formation with a translation region or polysome binding site of mRNA, suppression of gene expression by hybrid formation with a nucleic acid-protein interaction site, or the like.

The antisense nucleic acid against HVEM refers to, for example, a single-stranded nucleic acid complementary to some of base sequences selected from the gene sequence of HVEM described above, the base sequence encoding the amino acid sequence of HVEM described above, and the mRNA sequence of HVEM describe above. The nucleic acid may be a naturally occurring nucleic acid or an artificial nucleic acid, and may be based on either DNA or RNA. The length of the antisense nucleic acid usually ranges from about 15 bases to about the full length of mRNA, preferably from about 15 bases to about 30 bases. The complementarity of the antisense nucleic acid does not necessarily have to be 100%, and may be such that the antisense nucleic acid can complementarily bind to DNA or RNA encoding HVEM in vivo.

The siRNA (small interfering RNA) is an artificially-synthesized low-molecular-weight double-stranded RNA which is used for gene silencing through RNA interference (degradation of mRNA), and is used in the meaning including an siRNA expression vector which can supply the double-stranded RNA in vivo. The siRNA introduced into cells binds to an RNA-induced silencing complex (RISC). This complex binds to and cleaves mRNA having a sequence complementary to siRNA, thereby making it possible to sequence-specifically suppress gene expression. The siRNA can be prepared by synthesizing each of sense strand and antisense strand oligonucleotides using a DNA/RNA automatic synthesizer, and denaturing the oligonucleotides in appropriate annealing buffer at 90 to 95° C. for about 1 minute, and then annealing the denatured oligonucleotides at 30 to 70° C. for about 1 to 8 hours. The length of the siRNA is preferably 19 to 27 base pairs, more preferably 21 to 25 base pairs, or 21 to 23 base pairs.

The siRNA against HVEM can be designed based on its base sequence so as to cause degradation of mRNA transcribed from the HVEM gene (RNA interference). Examples of the siRNA which inhibits the expression of HVEM include siRNA which targets the mRNA sequence of HVEM described above.

The shRNA (short hairpin RNA) is an artificially-synthesized hairpin-type RNA sequence used for gene silencing through RNA interference (degradation of mRNA). The shRNA may be introduced into cells by a vector and expressed by a U6 promoter or H1 promoter, or may be prepared by synthesizing oligonucleotides having an shRNA sequence using a DNA/RNA automatic synthesizer and allowing the oligonucleotides to self-anneal by the same method as siRNA. The hairpin structure of the siRNA introduced into cells is cleaved into siRNA, which binds to an RNA-induced silencing complex (RISC). This complex binds to and cleaves mRNA having a sequence complementary to siRNA, thereby making it possible to sequence-specifically suppress gene expression.

The shRNA against HVEM can be designed based on its base sequence so as to cause degradation (RNA interference) of mRNA transcribed from the HVEM gene. Examples of the shRNA which inhibits the expression of HVEM include shRNA which targets the mRNA sequence of HVEM described above.

The miRNA (microRNA) is a functional nucleic acid which is encoded on the genome, undergoes a multi-step production process, and eventually becomes a microRNA of about 20 bases. The miRNA is classified as functional ncRNA (non-coding RNA: a general term for RNAs which are not translated into proteins), and plays an important role, in life phenomena, of regulating expression of other genes. In the present invention, the expression of the HVEM gene can be suppressed by introducing an miRNA having a specific base sequence into cells by a vector and administering the cells to a living body.

The gRNA (guide RNA) is an RNA molecule used in the genome editing technology. In the genome editing technology, the gRNA specifically recognizes a target sequence, guides binding of Cas9 protein to the target sequence, and enables knockout and knockin of a gene. In the present invention, the expression of the HVEM gene can be suppressed in vivo by administering a gRNA targeting the HVEM gene to a living body. The gRNA is used in the meaning including sgRNA (single guide RNA). Methods for designing gRNAs in the genome editing technology are widely known and can be appropriately designed by referring to, for example, Benchmarking CRISPR on-target sgRNA design, Yan et al., Brief Bioinform, 15 Feb. 2017.

The ribozyme is an RNA which has catalytic activity. While some of ribozymes have various activities, research on ribozymes as enzymes that cleave an RNA has made it possible to design ribozymes for the purpose of site-specific cleavage of RNAs. The ribozyme may have a size of 400 nucleotides or more, such as group I intron type or M1RNA included in RNase P, or may be a ribozyme having a size of about 40 nucleotides, which is called hammerhead type or hairpin type.

The aptamer includes a nucleic acid aptamer and a peptide aptamer. The nucleic acid aptamer and peptide aptamer used in the present invention can be obtained by using an in vitro molecular evolution method of forming complexes of library molecules and a target molecule in vitro and then screening them based on affinity, which is typified by the SELEX method (Systematic Evolution of Ligands by Exponential enrichment) or the mRNA display method.

The antisense nucleic acid, siRNA, shRNA, miRNA, ribozyme and nucleic acid aptamer may include various chemical modifications to improve stability and activity. For example, in order to prevent degradation by a hydrolase such as nuclease, their phosphate residues may be replaced with chemically modified phosphate residues such as phosphorothioate (PS), methylphosphonate, and phosphorodithioate. Alternatively, at least part of them may be composed of a nucleic acid analog such as a peptide nucleic acid (PNA).

The antibody against HVEM refers to an antibody which specifically binds to HVEM and inhibits the function of HVEM upon binding. In the present invention, any of a monoclonal antibody, a polyclonal antibody, a chimeric antibody, a humanized antibody, a human antibody, a mouse antibody, a rat antibody, a camel antibody, antibody fragments (for example, Fab, Fv, Fab', F (ab')$_2$, and ScFv) and the like may be used as the antibody, and these antibodies can be prepared according to a technique known to those skilled in the art. Usable antibodies against HVEM include the immunoglobulin single variable domain of the present invention, the antibody of the present invention and the immunoglobulin single variable domain multimer of the present invention, which will be described later.

The antibody against HVEM can be manufactured by using an HVEM protein or a part thereof as an antigen according to a known method for manufacturing an antibody or antiserum. The HVEM protein or a part thereof can be prepared by known protein expression method and purification method. Examples of the HVEM protein include, but are not limited to, human HVEM defined by the sequence information of HVEM described above. HVEM proteins derived from various organisms may be used as immunogens. The antibodies against HVEM which can be used in the present invention can also be prepared via a phage display method (see, for example, FEBS Letter, 441:20-24 (1998)).

The agents and compositions of the present invention are intended for use in treatment or prevention of a glioma. As used herein, the "glioma" is a general term for tumors developed from the neuroectodermal tissue of the brain parenchyma, accounts for 30 to 40% of primary intracranial tumors, and is the most frequent brain tumor. Examples of the glioma include oligodendroglioma, oligoastrocytoma, astrocytoma and glioblastoma multiforme. The "glioblastoma multiforme", which is also referred to as glioblastoma or anaplastic glioma, is a glioma composed mainly of undifferentiated cells derived from stellate cells. Glioblastoma multiforme exhibits prominent nuclear pleomorphism, and necrosis and vascular endothelial growth are found. Glioblastoma multiforme grows fast, infiltrates extensively, and is often developed in the adult cerebrum. Glioblastoma multiforme has been reported to be classified into four subtypes: proneural, neural, classical and mesenchymal (Verhaak R G et al., Cancer Cell, 17: 98-110 (2010)). As will be presented in the Examples below, HVEM is highly expressed in glioblastoma multiforme of the mesenchymal subtype, and thus the agents and compositions of the present invention can be preferably used in reduction of the risk of developing a glioma as will be described below (especially, glioblastoma multiforme of the mesenchymal subtype), in addition to treatment and prevention of glioblastoma multiforme (especially, glioblastoma multiforme of the mesenchymal subtype).

As will be prevented in the Examples below, proliferation of glioblastoma multiforme cells and neurosphere formation could be suppressed by inhibiting the expression of HVEM and the function of HVEM in the glioblastoma multiforme cells. In addition, signal transduction from APRIL via HVEM was observed to promote formation of a highly malignant brain tumor such as glioma. Therefore, the HVEM inhibitor, which is the active ingredient of the present invention, can be administered to a subject (for example, a brain tumor patient) whose HVEM expression amount exceeds an HVEM expression amount in a healthy subject or an HVEM expression amount in a normal tissue sample, particularly, a brain tumor patient in which HVEM is highly expressed in the brain. In addition, the target for treatment and prevention of the present invention can be an HVEM expression-dependent glioma or an HVEM ligand-dependent glioma. Whether the subject highly expresses HVEM, whether the glioma is HVEM-dependent, and whether the glioma is HVEM ligand-dependent can be evaluated, for example, for brain tissue excised during the brain surgery performed on the brain tumor patient, and details thereof can be determined according to the determining methods of the present invention which will be described below and the procedures which will be described in the Examples.

The agents and compositions of the present invention can also be administered to a subject at risk of developing a glioma (especially, glioblastoma multiforme), thereby reducing the risk of developing a glioma. As used herein, the "subject at risk of developing a glioma" means a subject who notices no symptoms of a glioma or who has not been diagnosed as having a glioma but is in danger of developing a glioma in the future. Examples of the subject includes brain tumor patients who have not been diagnosed as having a glioma and brain tumor patients who have undergone resection of brain tumor tissue. In addition, the "reduction of the risk of developing a glioma" means that the probability of developing a glioma is reduced, and the prognosis of a malignant brain tumor can be improved by reducing the probability of developing a glioma.

That is, according to another aspect of the present invention, there are provided an agent for reducing the risk of developing a glioma and a composition for use in reduction of the risk of developing a glioma, each comprising an HVEM inhibitor as an active ingredient, and also provided an agent for improving a prognosis in treatment of a malignant brain tumor and a composition for use in improvement of a prognosis in treatment of a brain tumor, each comprising an HVEM inhibitor as an active ingredient.

The agents and compositions of the present invention can be provided as pharmaceutical products or pharmaceutical compositions. The pharmaceutical products and pharmaceutical compositions of the present invention each comprise an HVEM inhibitor and a pharmaceutically acceptable carrier. The pharmaceutical products and pharmaceutical compositions of the present invention also include pharmaceutical products and pharmaceutical compositions intended for gene therapy. Such pharmaceutical products and pharmaceutical compositions comprise a nucleic acid targeting HVEM, such as an antisense nucleic acid, siRNA, shRNA, microRNA, gRNA, or a ribozyme as an active ingredient.

The pharmaceutical products and pharmaceutical compositions of the present invention may comprise an active ingredient other than the HVEM inhibitor, or may be used in combination with an active ingredient other than the HVEM inhibitor or a pharmaceutical product or pharmaceutical composition comprising the active ingredient. Examples of the active ingredient other than the HVEM inhibitor include anticancer agents (especially, anticancer agents intended for treatment of malignant brain tumors).

When the HVEM inhibitor, which is the active ingredient of the present invention, is administered to a subject, the administration route is not particularly limited as long as the effect for treating or preventing a glioma (especially, glioblastoma multiforme) can be obtained, but is preferably parenteral administration (for example, intravenous administration, local administration (including local administration using a catheter), subcutaneous administration, or intraperitoneal administration).

As a preparation for parenteral administration, an appropriate dosage form can be selected according to the specific administration form, and examples thereof include injections and suppositories. These formulations can be prepared using a pharmaceutically acceptable carrier by a technique commonly used in the art (for example, the known method described in the Japanese Pharmacopoeia, 15th Edition, General Regulations for Preparations). The pharmaceutically acceptable carrier includes excipients, binders, diluents, additives, perfumes, buffers, thickeners, colorants, stabilizers, emulsifiers, dispersants, suspending agents, and preservatives.

The dose of the HVEM inhibitor in the present invention can be determined depending on the type of active ingredient, the sex, age and body weight of the subject to which the HVEM inhibitor is administered, symptoms, dosage form, administration route, and the like. In the present invention, when the HVEM inhibitor is administered for the purpose of treating or preventing a glioma (especially, glioblastoma multiforme), the single dose of the HVEM inhibitor for an adult can be determined, for example, in the range of from 0.0001 mg to 1000 mg/kg of body weight, but is not limited thereto. The daily dose of the HVEM inhibitor for an adult can be determined depending on the type of active ingredient, the sex, age and body weight of the subject to which the HVEM inhibitor is administered, symptoms, dosage form, administration route, and the like. For example, the dose of the active ingredient can be administered once daily or divided into 2 to 4 parts. The agents and compositions of the present invention can be administered not only to humans in need thereof, but also to non-human mammals (e.g., mice, rats, rabbits, dogs, cats, cows, horses, pigs, sheep, goats, and monkeys).

Marker for Malignancy of Brain Tumor and Prognostic Marker for Brain Tumor

As will be described in the Examples below, it was shown that high expression of HVEM correlates with a brain tumor, especially glioblastoma multiforme belonging to the mesenchymal subtype, and that high expression of HVEM correlates with a poor prognosis for a glioblastoma patient. It was also confirmed that overexpression of HVEM promotes proliferation of glioblastoma multiforme cells, neurosphere formation and in vivo tumor growth. Thus, according to the present invention, there are provided a marker for malignancy of a brain tumor consisting of an HVEM protein or an HVEM gene and a prognostic marker for a brain tumor consisting of an HVEM protein or an HVEM gene. The marker for malignancy of a brain tumor of the present invention can be used to determine malignancy of a brain tumor in a brain tumor patient, and can also be used to determine a glioma (especially, glioblastoma multiforme). The prognostic marker for a brain tumor of the present invention can be used to predict or estimate a prognosis for a brain tumor patient in treatment of a brain tumor. Therefore, these markers of the present invention are useful as indicators in determining the treatment policy for a brain tumor.

In order to use the markers of the present invention in diagnosis of human patients, the HVEM protein or HVEM gene is preferably derived from a human. Further, in the markers of the present invention, the HVEM gene may be a DNA consisting of the genome sequence of the HVEM gene, or may be the mRNA of the HVEM gene or a cDNA obtained by reverse transcription of the mRNA of the HVEM gene. The markers of the present invention can be implemented according to the method for determining malignancy of a brain tumor of the present invention and the method for determining a prognosis for a brain tumor patient of the present invention.

Methods for Determining Malignancy and Prognosis of a Brain Tumor

According to another aspect of the present invention, there is provided a method for determining malignancy of a brain tumor, the method comprising the step of measuring an HVEM expression amount in a biological sample of a subject (especially, brain tumor patient).

In the present invention, the "biological sample" means a sample separated from a living body, and examples thereof include brain tissue excised during brain surgery.

In the method for determining the malignancy of the present invention, first, the step (A) of measuring an HVEM expression amount in a biological sample of a subject to be tested is carried out. The HVEM expression amount can be measured in vitro by a known method.

For example, the HVEM expression amount in a biological sample can be measured based on the expression amount of the HVEM protein. In this case, the expression amount of the HVEM protein can be measured by a known detection means using a specific binding substance to the HVEM protein, and can be measured by, for example, ELISA, Western blotting, immunohistochemical staining or the like. Examples of the specific binding substance to the HVEM protein include antibodies, and those described for the agents and compositions of the present invention and the antibodies of the present invention can be used.

The HVEM expression amount in a biological sample can also be measured based on the expression amount of the HVEM gene. In this case, the expression amount of the HVEM gene can be measured by a known method such as RT-PCR, quantitative RT-PCR, DNA microarray analysis, Northern blotting or the like. The probe and primer set used in measurement of the expression amount of the HVEM gene can be prepared based on the sequence information of the HVEM gene described above with reference to the Examples described later.

In the method for determining the malignancy of the present invention, the step of determining a degree of malignancy of the tumor cell contained in the biological sample based on the HVEM expression amount measured in the step (A) can further be carried out. In this step, when the HVEM expression amount in the biological sample of the subject exceeds the HVEM expression amount in a biological sample of a healthy subject or in a normal tissue sample (preferably, with a significant difference), it is shown that the biological sample contains a highly malignant tumor cell population (for example, glioma cells, especially, glioblastoma multiforme cells). That is, the method for determining the malignancy of the present invention may further comprise the step (B1) of, when the HVEM expression amount in the biological sample of the subject exceeds the HVEM expression amount in a biological sample of a healthy subject or in a normal tissue sample (preferably, with a significant difference), determining that the biological sample contains a highly malignant tumor cell population.

In the method for determining the malignancy of the present invention, the step of determining malignancy of a brain tumor for the subject from which the biological sample has been collected, based on the HVEM expression amount measured in the step (A) can further be carried out. In this step, it is indicated that the subject suffers from a highly malignant brain tumor (for example, glioma, especially, glioblastoma multiforme) if the HVEM expression amount in the biological sample of the subject exceeds the HVEM expression amount in a biological sample of a healthy subject or in a normal tissue sample (preferably, with a significant difference). That is, the method for determining the malignancy of the present invention may further comprise the step (B2) of, when the HVEM expression amount in the biological sample of the subject exceeds the HVEM expression amount in a biological sample of a healthy subject or in a normal tissue sample (preferably, with a significant difference), determining that the subject suffers from a highly malignant brain tumor.

In the present invention, the HVEM expression amount in a biological sample of a healthy subject or in a normal tissue sample (cutoff value) can be an average value calculated by measuring HVEM expression amounts in biological samples preliminarily collected from a plurality of healthy subjects or in normal tissues preliminarily collected from a plurality of subjects (including brain tumor patients), or can be a value calculated according to the following equation (1).

Cutoff value=(average value of HVEM expression amount in biological sample of healthy subject or in normal tissue sample)±k×(standard deviation of HVEM expression amount in biological sample of healthy subject or in normal tissue sample)                    Equation (1)

wherein k is a constant of 0 to 3, preferably k=1 to 3, and, particularly, can be 2.

According to the method for determining the malignancy of the present invention, a highly malignant tumor cell population such as glioma cells can be detected in the biological sample to be tested. According to the method for determining the malignancy of the present invention, a highly malignant brain tissue such as a glioma can be detected in the subject. Therefore, the method for determining the malignancy of the present invention is useful in that the method provides a material for judging the treatment policy for a brain tumor. That is, the method for determining the malignancy of the present invention can be adjunctively used in diagnosis and/or differentiation of a glioma (especially, glioblastoma multiforme), and whether the subject suffers from a glioma can be ultimately judged, by the doctor, in combination with other findings.

According to another aspect of the present invention, there is provided a method for determining a prognosis for a brain tumor patient, the method comprising the step of measuring an HVEM expression amount in a biological sample of a subject (especially, brain tumor patient).

In the method for determining the prognosis of the present invention, first, the step (C) of measuring an HVEM expression amount in a biological sample of a subject to be tested is carried out. The HVEM expression amount can be measured in the same manner as the method for determining the malignancy of the present invention.

In the method for determining the prognosis of the present invention, the step of determining a prognosis for the subject from which the biological sample has been collected, based on the HVEM expression amount measured in the step (C), can further be carried out. In this step, it is indicated that the subject has a poor prognosis if the HVEM expression amount in the biological sample of the subject exceeds the HVEM expression amount in a biological sample of a healthy subject or in a normal tissue sample (preferably, with a significant difference). That is, the method for determining the malignancy of the present invention may further comprise the step (D) of, when the HVEM expression amount in the biological sample of the subject exceeds the HVEM expression amount in a biological sample of a healthy subject or in a normal tissue sample (preferably, with a significant difference), determining that the subject has a poor prognosis. The HVEM expression amount in a biological sample of a healthy subject or in a normal tissue sample (cutoff value) can be an average value calculated by measuring HVEM expression amounts in biological samples preliminarily collected from a plurality of healthy subjects or in normal tissues preliminarily collected from a plurality of subjects (including brain tumor patients), or can be a value calculated according to the above equation (1). In addition, in the method for determining the malignancy of the present invention, poor prognosis means that the survival rate within a predetermined period is lower and that there is a high probability of developing a highly malignant brain tumor (for example, glioma, particularly, glioblastoma multiforme).

The method for determining the prognosis of the present invention can be used to predict or estimate a prognosis for a brain tumor patient in treatment of a brain tumor. Therefore, the method for determining the prognosis of the present invention is useful in that the method provides a material for judging the treatment policy for a brain tumor. That is, the method for determining the prognosis of the present invention can be adjunctively used in diagnosis and/or differentiation of a glioma (especially, glioblastoma multiforme), and whether the prognosis for the subject is poor or good can be ultimately judged, by the doctor, in combination with other findings.

Single Variable Domain and Antibody

According to the present invention, there is provided an immunoglobulin single variable domain which specifically binds to HVEM and suppresses tumor growth (especially, proliferation of malignant tumor cells). The single variable domain of the present invention can bind to HVEM at an EC50 value of less than 80 nM.

The single variable domain of the present invention can be characterized by complementarity determining regions 1 to 3 (CDR1, CDR2 and CDR3), and CDR1, CDR2 and CDR3 can be identified by a combination of CDR1, CDR2 and CDR3 selected from the group consisting of the above (i), (ii), (iii), (iv), (v), (vi) and (vii).

The single variable domain of the present invention can also be characterized by framework regions 1 to 4 (FR1, FR2, FR3 and FR4), and FR1, FR2, FR3 and FR4 can be identified by a combination of FR1, FR2, FR3 and FR4 selected from the group consisting of the above (viii), (ix), (x), (xi), (xii), (xiii) and (xiv). The single variable domain of the present invention can be identified by the complementarity determining regions 1 to 3 and the framework regions 1 to 4, and, in this case, the single variable domain of the present invention can be composed of FR1-CDR1-FR2-CDR2-FR3-CDR3-FR4 linked from the N-terminal side in this order.

When CDR1, CDR2 and CDR3 of the single variable domain of the present invention are the above combination (i), the above combination (viii) can be selected as the combination of FR1, FR2, FR3 and FR4. When CDR1, CDR2 and CDR3 of the single variable domain of the present invention are the above combination (ii), the above combination (ix) can be selected as the combination of FR1, FR2, FR3 and FR4. When CDR1, CDR2 and CDR3 of the single variable domain of the present invention are the above combination (iii), the above combination (x) can be selected as the combination of FR1, FR2, FR3 and FR4. When CDR1, CDR2 and CDR3 of the single variable domain of the present invention are the above combination (iv), the above combination (xi) can be selected as the combination of FR1, FR2, FR3 and FR4. When CDR1, CDR2 and CDR3 of the single variable domain of the present invention are the above combination (v), the above combination (xii) can be selected as the combination of FR1, FR2, FR3 and FR4. When CDR1, CDR2 and CDR3 of the single variable domain of the present invention are the above combination (vi), the above combination (xiii) can be selected as the combination of FR1, FR2, FR3 and FR4. When CDR1, CDR2 and CDR3 of the single variable domain of the present invention are the above combination (vii), the above combination (xiv) can be selected as the combination of FR1, FR2, FR3 and FR4.

The single variable domain of the present invention can also be identified by the single variable domain sequenced in the Examples (the above polypeptide (xv)), but, in the present invention, in addition to this, a polypeptide which is substantially identical with the above polypeptide (xv) is also included in the single variable domain of the present invention.

An example of the polypeptide which is substantially identical with the single variable domain of the present invention is a humanized single variable domain. A method for humanizing a single variable domain is known. For example, a humanized single variable domain can be obtained by comparing the sequences of the framework regions of the amino acid sequence of a naturally occurring single variable domain with the corresponding framework sequences of the amino acid sequences of one or more closely-related human single variable domains to confirm potentially useful humanization replacements, and then introducing the one or more potentially useful humanization replacements thus determined into the amino acid sequence of the single variable domain of the present invention. The humanized single variable domain thus obtained can be subjected to confirmatory tests for affinity for the target, stability and other desired properties to determine the amino acid sequence of an appropriate humanized single variable domain.

The polypeptide which is substantially identical with the single variable domain of the present invention can be represented by a polypeptide selected from the above (xvi) and (xvii).

In the above (xvi), the "identity" is used in the meaning including "homology". As used herein, the "identity" is, for example, a degree of identity when the sequences to be compared are appropriately aligned, and means the appearance rate (%) of an accurate amino acid match between the sequences. For identity, for example, the presence of gaps in the sequences and the properties of the amino acids are considered (Wilbur, Natl. Acad. Sci. U.S.A. 80:726-730 (1983)). The alignment can be performed, for example, by using an arbitrary algorithm, and specifically, BLAST (Basic local alignment search tool) (Altschul et al., J. Mol. Biol. 215:403-410 (1990)), FASTA (Peasron et al., Methods in Enzymology 183:63-69 (1990)), Smith-Waterman (Meth. Enzym., 164, 765 (1988)) and other homology search software can be used. In addition, the identity can be calculated using, for example, a known homology search program as indicated above, and, for example, can be calculated using default parameters in the homology algorithm BLAST of the National Center for Biotechnology Information (NCBI).

The identity in the above (xvi) can be 80% or more, 85% or more, 90% or more, 95% or more, 96% or more, 97% or more, 98% or more, or 99% or more.

In the above (xvii), the sentence that "one or more amino acids is/are deleted, substituted, inserted and/or added in the amino acid sequence" means that a number of amino acids produced by a known method such as site mutagenesis, or a number of naturally occurring amino acids have been modified by deletion, substitution, insertion and/or addition. The number of amino acids modified by the substitution or the like is, for example, 1 to 20, 1 to 15, 1 to 10, 1 to 5, 1 to 4, 1 to 3, 1 to 2, or 1. In the amino acid sequence, the modifications may occur continuously or discontinuously, for example.

Examples of the insertion of an amino acid in the above (xvii) include an insertion into the amino acid sequence. Further, the addition of an amino acid in the (xvii) may be, for example, an addition to the N-terminal or C-terminal of the amino acid sequence, or an addition to both the N-terminal and the C-terminal.

The substitution of an amino acid in the above (xvii) means that an amino acid residue constituting the amino acid sequence is substituted with another type of amino acid residue. The substitution of an amino acid in the above (xvii) may be, for example, a conservative substitution. The "conservative substitution" means substituting one or more amino acids with another/other amino acid(s) and/or amino acid derivative(s) so as not to substantially modify the function of the protein. In the conservative substitution, the amino acid to be substituted and the amino acid after substitution are preferably similar, for example, in properties and/or function. Specifically, they are preferably similar in chemical properties such as indicators of hydrophobicity and hydrophilicity, polarity and charge, or physical properties such as secondary structure. Thus, amino acids or amino acid derivatives having similar properties and/or functions are known in the art. Examples of non-polar amino acids (hydrophobic amino acids) include alanine, valine, isoleucine, leucine, proline, tryptophan, phenylalanine, and methionine. Examples of polar amino acids (neutral amino acids) include glycine, serine, threonine, tyrosine, glutamine, asparagine, and cysteine. Examples of positively-charged amino acids (basic amino acids) include arginine, histidine, and lysine, and examples of negatively-charged amino acids (acidic amino acids) include aspartic acid and glutamic acid.

A preferred amino acid modification in the above (xvii) is, for example, one amino acid substitution, two amino acid substitution, three amino acid substitution, four amino acid substitution, five amino acid substitution, six amino acid substitution, or seven amino acids substitution, and a modification in which the substitution is a conservative substitution is more preferred. A preferred amino acid modification in the above (xvii) is, for example, a modification which has occurred in the framework regions 1 to 4, and a modification which has occurred only in the framework regions 1 to 4 is more preferred. A preferred amino acid modification in the above (xvii) is, for example, a modification which is one amino acid substitution, two amino acid substitution, three amino acid substitution, four amino acid substitution, five amino acid substitution, six amino acid substitution, or seven amino acids, and has occurred in the framework regions 1 to 4. A modification which is one amino acid substitution, two amino acid substitution, three amino acid substitution, four amino acid substitution, five amino acid substitution, six amino acid substitution, or seven amino acids, and has red only in the framework regions 1 to 4 is more preferred.

According to another aspect of the present invention, there are provided an antibody and an immunoglobulin single variable domain multimer, each comprising the immunoglobulin single variable domain of the present invention. Such an antibody includes a so-called heavy chain antibody (or VHH antibody) composed only of two heavy chains as variable regions. Further, the multimer includes a complex in which a plurality of the single variable domains of the present invention bind to each other directly or via a linker, and one or more optional components (e.g., a physiologically active peptide and a stabilizing substance) other than the single variable domain of the present invention may be further linked to such a complex.

The single variable domain, antibody and multimer of the present invention can be manufactured, for example, by expressing polynucleotides encoding them in a host and recovering expression products. Thus, according to yet another aspect of the present invention, there are provided a polynucleotide encoding the single variable domain, antibody or multimer of the present invention, and a host cell obtained by introducing the polynucleotide of the present invention or a vector to which the polynucleotide of the present invention is operably linked. The "polynucleotide encoding the single variable domain or the like" can be identified based on the genetic code (that is, codon) based on the amino acid sequence of the single variable domain or the like. In the present invention, the "polynucleotide" includes DNA and RNA, and further includes modified products thereof and artificial nucleic acids, but DNA is preferred. Also, the DNA includes cDNA, genomic DNA and chemically-synthesized DNA.

The polynucleotide of the present invention is not particularly limited as long as it can be expressed in the host to be used and is composed of codons encoding the single variable domain or the like having HVEM binding activity. In order to enable expression of the polynucleotide in the host to be used or to increase the expression amount, the codons may be optimized. The codons can be optimized by a known method commonly used in the art.

The single variable domain or the like of the present invention can be expressed in various host cells such as bacterial cells, molds, animal cells, plant cells, baculovirus/insect cells or yeast cells. An expression vector for expressing the single variable domain or the like of the present invention is known, and vectors suitable for various host cells can be used.

When the single variable domain or the like expressed in the host is extracted from cultured bacterial cells or cultured cells, after culturing, the bacterial cells or cultured cells are collected by a known method, suspended in appropriate buffer, destroyed by ultrasonic waves, lysozyme and/or freeze thawing, and then subjected to centrifugation or filtration to obtain a soluble extract, and the target single variable domain or the like can be obtained from the obtained extract using an appropriate combination of known separation and purification methods. As known separation and purification methods, there can be used a method of utilizing solubility, such as salting-out or solvent precipitation; a method of mainly utilizing a difference in molecular weight, such as dialysis, ultrafiltration, gel filtration or SDS-PAGE; a method of utilizing a difference in charge, such as ion exchange chromatography; a method of utilizing a specific affinity, such as affinity chromatography; a method of utilizing a difference in hydrophobicity, such as reverse phase high performance liquid chromatography; and a method of utilizing a difference in isoelectric point, such as an isoelectric point electrophoresis.

The single variable domain, antibody or multimer of the present invention has HVEM binding activity and can suppress tumor growth. Since substances which inhibit the expression of HVEM and substances which inhibit the function of HVEM can be used in treatment or prevention of a glioma as described above, the single variable domain, antibody or multimer of the present invention can be used as an active ingredient of a pharmaceutical composition, and, in particular, can be used as an active ingredient of the agents and compositions of the present invention (that is, agents for treating and preventing a glioma).

Other Aspects of the Present Invention

According to another aspect of the present invention, there is provided a method for treating or preventing a glioma, comprising the step of administering an effective amount of an HVEM inhibitor to a subject in need thereof. Also, according to another aspect of the present invention, there is provided a method for reducing the risk of developing a glioma, comprising the step of administering an effective amount of an HVEM inhibitor to a subject in need thereof. Also, according to another aspect of the present invention, there is provided a method for improving a prognosis in treatment of a malignant brain tumor, comprising the step of administering an effective amount of an HVEM inhibitor to a subject in need thereof. The methods of the present invention can be carried out according to the descriptions regarding the agents and compositions of the present invention.

According to another aspect of the present invention, there is provided a method for treating a malignant tumor or glioma, comprising: carrying out the method for determining the malignancy of the present invention; and administering an effective amount of an anticancer agent (for example, an anticancer agent intended for treatment of a malignant brain tumor, preferably an HVEM inhibitor, especially, a substance which inhibits binding between HVEM and APRIL) to a subject determined to suffer from, or to be highly likely to suffer from, a highly malignant brain tumor (or a subject determined to suffer from, or to be highly likely to suffer from, a glioma). The method of the present invention can be carried out according to the descriptions regarding the method for determining the malignancy of the present invention and the descriptions regarding the agents and compositions of the present invention.

According to another aspect of the present invention, there is provided use of an HVEM inhibitor, for manufacture of an agent for treating or preventing a glioma, or as an agent for treating or preventing a glioma. Also, according to another aspect of the present invention, there is provided use of an HVEM inhibitor, for manufacture of an agent for reducing the risk of developing a glioma, or as an agent for reducing the risk of developing a glioma. Also, according to another aspect of the present invention, there is provided use of an HVEM inhibitor, for manufacture of an agent for improving a prognosis in treatment of a malignant brain tumor, or as an agent for improving a prognosis in treatment of a malignant brain tumor. The uses of the present invention can be carried out according to the descriptions regarding the agents and compositions of the present invention.

According to another aspect of the present invention, there is provided an HVEM inhibitor, as an agent for treating or preventing a glioma, for use in treatment or prevention of a glioma, or for use in the treating or preventing method of the present invention. Also, according to another aspect of the present invention, there is provided an HVEM inhibitor, as an agent for reducing the risk of developing a glioma, for use in reduction of the risk of developing a glioma, or for use in the risk reducing method of the present invention. Also, according to another aspect of the present invention, there is provided an HVEM inhibitor, as an agent for improving a prognosis in treatment of a malignant brain tumor, or for use in improvement of a prognosis in treatment of a malignant brain tumor, or for use in the prognosis improving method of the present invention. The HVEM inhibitor can be carried out according to the descriptions regarding the agents and compositions of the present invention.

The methods and uses of the present invention may be uses in mammals including humans, and are intended to involve both of therapeutic use and non-therapeutic use. The "non-therapeutic," as used herein, means elimination of operating, treating or diagnosing activities to a human (i.e., medical activities to a human), and specifically means elimination of a method of performing operation or treatment of, or diagnosis involving, a human by a doctor or a person who receives an instruction from the doctor.

EXAMPLES

Hereinafter, the present invention will be described in more detail by way of the following examples, but is not limited thereto.
Database
Repository for Molecular Brain Neoplasia Data (REM-BRANDT) and The Cancer Genome Atlas (TCGA) were extracted from Project Betastasis, TCGA data portal, and NIH's Genome Data Commons.

Statistical Analysis

Statistical analyses (Welch's t-test, Student's t-test, two-way analysis of variance, Kruskal-Wallis test, and logrank test) were performed by statistical software R.

Example 1: Inhibitory Effect of BMP-4 on Proliferation of GBM Cell Strain and Neurosphere Formation (1) Culture Conditions for Human Glioblastoma Cell Human glioblastoma multiforme cells, i.e., U3024MG, U3031MG and U3054MG cell strains, were obtained from the Human Glioblastoma Cell Culture resource (sometimes referred to simply as "HGCC" herein), and maintained under conditions for maintaining characteristics (Xie Y et al., EBioMedicine, 2:1351-63(2015)) of glioma-initiating cells (sometimes referred to simply as "GIC" herein). Specifically, the cell strains were cultured in DMEM/F12 (manufactured by Thermo Fisher Scientific Inc.) and NEU-ROBASAL® Media (manufactured by Thermo Fisher Scientific Inc.) which were enriched with B-27© Supplement (manufactured by Thermo Fisher Scientific Inc.), N-2 supplement (manufactured by Thermo Fisher Scientific Inc.), 20 ng/mL of epidermal growth factor (EGF, manufactured by PeproTech, Inc.), and Fibroblast Growth Factor-basic (bFGF, manufactured by PeproTech, Inc.).

(2) BMP-4 Treatment

To the cells prepared in the above item (1), 30 ng/mL of recombinant human BMP-4 (manufactured by R & D Systems, Inc.) was added. In addition, a group to which the BMP-4 was not added was prepared as a control.

(3) In Vitro Cell Proliferation Assay

The cells prepared in the above item (2) were cultured for 7 days, and an in vitro cell proliferation assay was performed. Cell Count Kit-8 (manufactured by Nacalai Tesque, Inc.) was used according to the manufacturer's instructions. The number of cells was measured by measuring the absorbances at 450 nm and 595 nm using a microplate reader (Model 680, manufactured by Bio-Rad Laboratories, Inc.) or Enspire (manufactured by PerkinElmer, Inc.).

(4) Sphere Formation Assay

The cells prepared in the above item (2) were seeded on an ultra-low adhesion microplate (manufactured by Corning Inc.) at a density of 1 to 100 cells/well, and cultured for 7 days. Cell clusters having a diameter of 20 μm or more were regarded as spheres. Wells without spheres were counted in each condition.

(5) Results

The results were as shown in FIG. 1. BMP-4 was found to strongly inhibit proliferation of U3024MG and U3031MG cells, in the cell proliferation assay under serum-free conditions and neurosphere formation (Lenkiewicz M. et al., Curr Protoc Stem Cell Biol., Chapter 3: Unit3.3 (2009)). In contrast, BMP-4 was confirmed not to inhibit proliferation of U3054MG cells or sphere formation.

Example 2: Search for BMP-4 Target Gene (1) RNA Sequence Analysis

RNA sequence analysis was performed to identify BMP target genes using human glioblastoma cells TGS-04 (Raja E. et al., Oncogene, 36:4963-4974 (2017)). Expression amounts of genes controlled by BMP-4 stimulation in the RNA sequence data were analyzed based on their FPKM value (fragments per kilobase of exon per million fragments), and genes whose FPKM value was suppressed to ½ or less by BMP-4 stimulation were extracted. Furthermore, genes encoding transmembrane proteins were searched from among the extracted genes. As a result, it was confirmed that the expression of HVEM was suppressed to ½ or less by BMP-4 in the TGS-04 cells (data not shown).

(2) Quantitative Real-Time (RT)-PCR Analysis

Total RNA was extracted from the GBM cells prepared in Example 1 (2) (U3024MG cells or U3031MG cells) using RNEASY® Mini Kit (manufactured by Qiagen), and the expression of human HVEM and human GAPDH (used for standardization of relative expression amounts) was analyzed. The primers used for quantitative RT-PCR are indicated in Table 1. Complementary DNA was synthesized using PRIMESCRIPT® II 1st Strand cDNA Synthesis Kit (manufactured by Takara Bio Inc.). The gene expression level was quantified by STEP ONE PLUS® Real-Time PCR Systems (manufactured by Applied Biosystems) using FASTSTART® Universal SYBR® Green Master Mix (manufactured by Roche).

[Table 1]

TABLE 1

| Primer set used in quantitative RT-PCR | | | | |
|---|---|---|---|---|
| Species | Target gene | Forward/ reverse | Sequence (5' → 3') | SEQ ID NO: |
| Homo sapiens | GAPDH | Forward | GAAGGTGAAGGTCGGAGTC | 1 |
| Homo sapiens | GAPDH | Reverse | GAAGATGGTGATGGGATTTC | 2 |
| Homo sapiens | HVEM | Forward | GTGTCTGCAGTGCCAAATGT | 3 |
| Homo sapiens | HVEM | Reverse | CCACACACGGCGTTCTCT | 4 |

Figure 2:
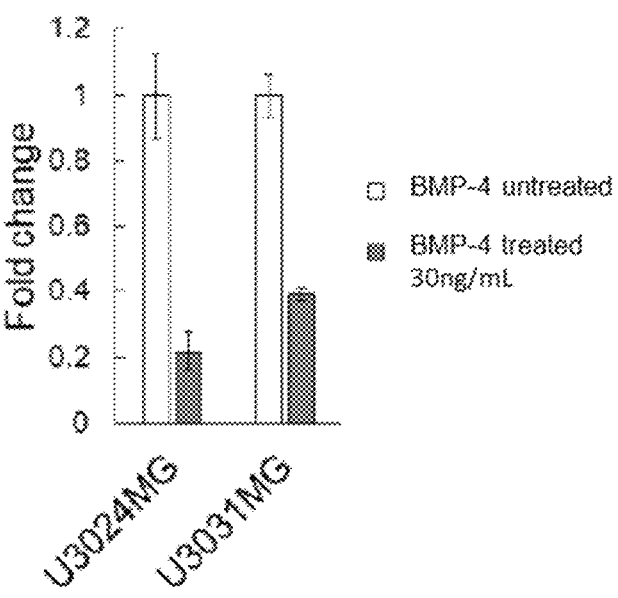
FIG. 2 is a diagram showing quantitative RT-PCR analysis of HVEM in GBM cells treated with BMP-4 in Example 2.

The results were as shown in FIG. 2. In U3024MG cells and U3031MG cells, the expression of HVEM was strongly suppressed by BMP-4.

Example 3: Correlation Between HVEM Expression and Poor Prognosis for GBM Patient The following expressions (1) to (4) were analyzed using The National Cancer Institute Genomic Data Commons (sometimes referred to simply as "GDC" herein) TCGA brain tumor data set.

(1) Expression of HVEM in GBM

Figure 3:
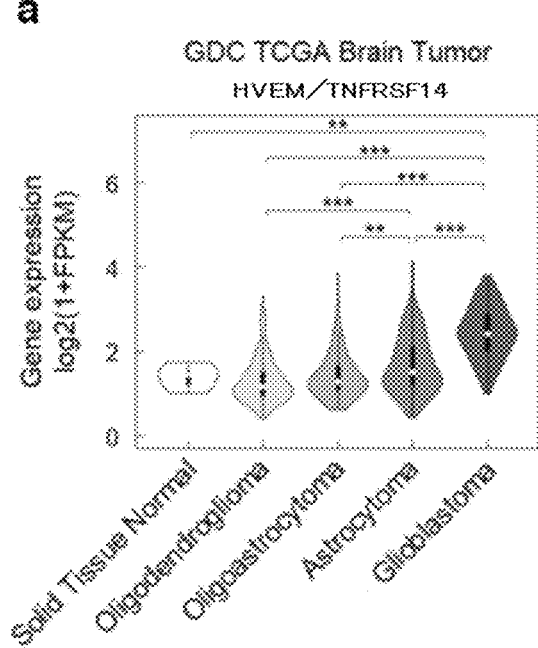
FIG. 3a is a diagram showing that expression levels of HVEM increase in malignant brain tumors in Example 3. Expression levels of HVEM in normal brain and brain tumor tissues in the TCGA dataset (P<0.01, *P<0.001; two-tailed Kruskal-Wallis test with Bonferroni's correction).
FIG. 3b is a diagram showing that, in Example 3, the expression levels of HVEM increase in malignant brain tumors and correlate with prognoses of brain tumor patients. Kaplan-Meier plots of the brain tumor patients in the TCGA dataset. Low-malignancy gliomas include oligodendroglioma, oligoastrocytoma, and astrocytoma. The patients were equally divided into two groups based on the HVEM expression levels.
FIGS. 3c and 3d are diagrams showing that, in Example 3, the expression levels of HVEM increase in malignant brain tumors and correlate with prognoses of brain tumor patients. (c) Expression levels of HVEM in the GBM subtypes in the TCGA dataset (P<0.01, *P<0.001; two-tailed Kruskal-Wallis test with Bonferroni's correction). (d) The expression levels of HVEM in human neural stem cells (hNSCs) and the four subtypes of human GBM cells were determined by quantitative RT-PCR. Data is indicated as mean±SD (n=3 biological replicates). The GBM cells were classified into the four GBM subtypes according to the data obtained by the AFFYMETRIX GENECHIP® Human Exon 1.0 ST Array (Xie Y et al., EBioMedicine, 2: 1351-63 (2015)).
Figure 3:
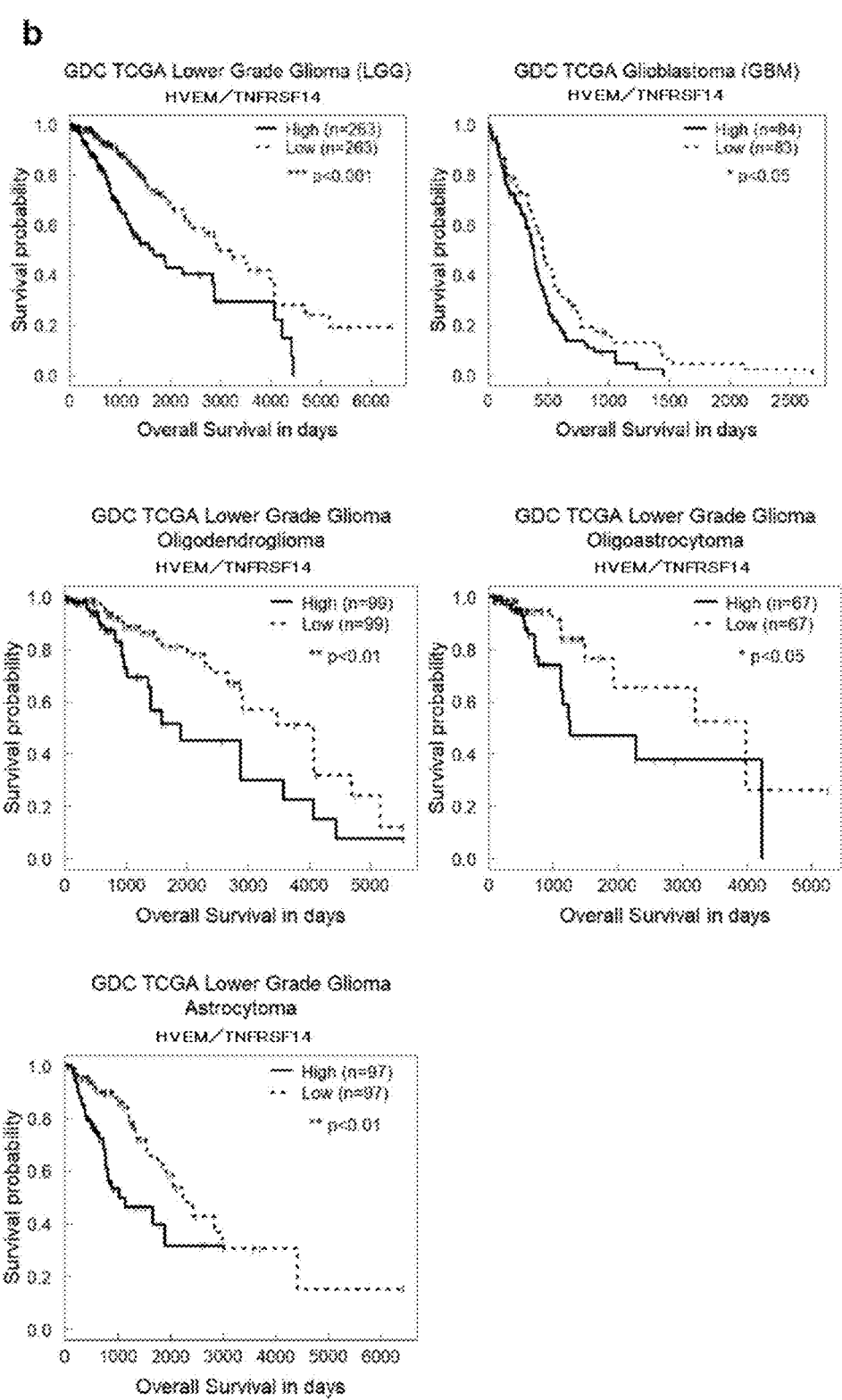
Figure 3:
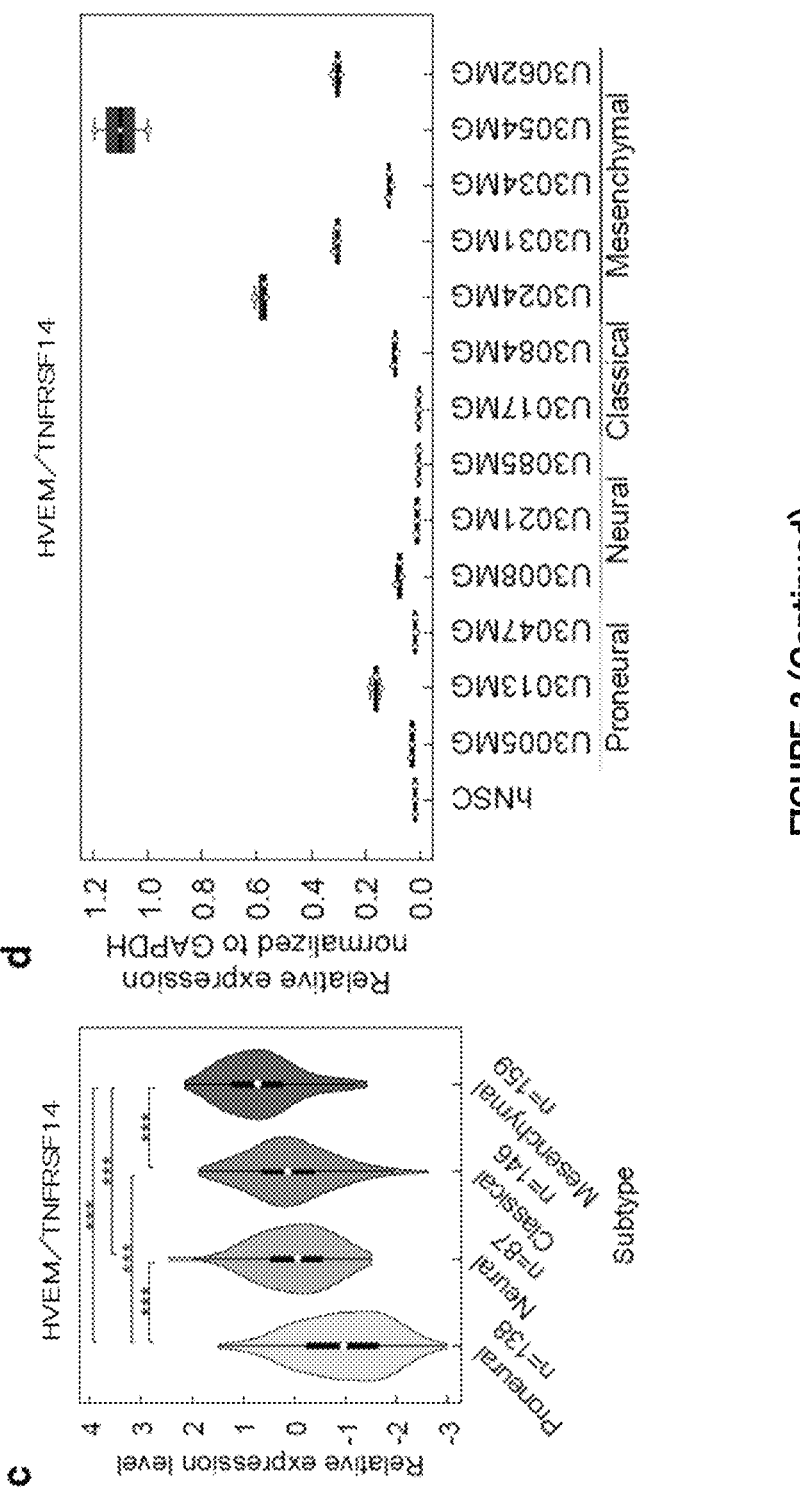

To investigate the function of HVEM in brain tumors, the expression level of HVEM mRNA was analyzed using the GDC TCGA dataset. The results were as shown in FIG. 3a. Significantly increased expression of HVEM was observed in GBM, as compared with the expression thereof in normal brain tissue and low-malignancy glioma tissues such as oligodendroglioma, oligoastrocytoma and astrocytoma. No significant difference was observed between the expression levels in normal brain and low-malignancy glioma. However, significantly increased expression of HVEM was observed in astrocytoma, as compared with the expression thereof in oligodendroglioma and oligoastrocytoma.

(2) Survival of Brain Tumor Patient and Expression of HVEM

Survival of brain tumor patients was analyzed using the GDC TCGA dataset. The results were as shown in FIG. 3b. GBM patients having low expression of HVEM in their tumors were observed to have a significantly long survival time as compared with patients having high expression of HVEM, and similar results were confirmed also in patients with lower grade glioma (LGG), oligodendroglioma, oligoastrocytoma and astrocytoma.

(3) Expression of HVEM in GBM Subtype

The expression of HVEM in four subtypes of GBM (proneural, neural, classical and mesenchymal, based on the classification of Verhaak et al., Cancer Cell, 17:98-110 (2010)) was analyzed. The results were as shown in FIG. 3c. The highest expression of HVEM was observed in the mesenchymal subtype, but the lowest expression was observed in the proneural subtype.

(4) Expression of HVEM in GBM Subtype

The expression of HVEM in 13 different GBM cell strains (obtained from HGCC resource (Xie Y et al., EBioMedicine, 2:1351-63 (2015)) and H9 hESC-derived human neural stem cells (hNSC, manufactured by Thermo Fisher Scientific Inc.) was analyzed by quantitative RT-PCR. In addition, hNSC was cultured in KnockOut DMEM/F12 (manufactured by Thermo Fisher Scientific Inc.) supplemented with StemPro nerve supplement (manufactured by Thermo Fisher Scientific Inc.), EGF (20 ng/mL) and bFGF (20 ng/mL). For the cells, the primers used were SEQ ID NOs: 1 to 4 shown in Table 1, and RT-PCR was performed according to the method described in Example 2 (2). The results were as shown in FIG. 3d. High expression of HVEM was observed in all the 5 strains of the mesenchymal subtype. In contrast, only one of the 2 to 3 strains tested in each of the proneural, neural and classical subtypes showed increased HVEM expression, and the HVEM expression level in the mesenchymal subtype was confirmed to be generally higher than that in the other subtypes. From these results, it was shown that the HVEM expression increased in specific human brain tumors, especially, the mesenchymal subtype of GBM, and that high expression of HVEM correlates with a poor prognosis for glioblastoma patients.

Example 4: Suppression of Proliferation of GBM Cell and Neurosphere Formation by Inhibition of HVEM (1) Inhibition of HVEM by shRNA The DNA sequences encoding the short hairpin RNAs (shRNAs) indicated in Table 2 were each inserted into the pENTR4-H1 or pENTR4-mU6 vector. An LR reaction between the pENTR4-H1 and CS-RfA-CMV-PuroR vectors or between pENTR4-mU6 and CS-RfA-CG was catalyzed by LR CLONASE® (manufactured by Thermo Fisher Scientific Inc.). The vector plasmids pCAG-HIVgp and pCMV-VSV-G-Rev were transduced into HEK293FT cells using LIPOFECTAMINE® 2000 (manufactured by Thermo Fisher Scientific Inc.). Lentivirus particles were concentrated with LENTI-X® concentrator (manufactured by Takara Bio Inc.) and then reconstituted with serum-free buffer.

[Table 2]

TABLE 2

| | | shRNA sequence | |
| --- | --- | --- | --- |
| Species | shRNA | Target sequence of shRNA (5' → 3') | SEQ ID NO: |
| | Control shRNA #1 | GUGGUUUACAUGUCGACUAA | 5 |
| | Control shRNA #2 | AUGGUUUACAUGUUGUGUGA | 6 |

TABLE 2-continued

| | | shRNA sequence | |
| --- | --- | --- | --- |
| Species | shRNA | Target sequence of shRNA (5' → 3') | SEQ ID NO: |
| Homo sapiens | HVEM shRNA #1 | GUGCAGUCCAGGUUAUCGUGU | 7 |
| Homo sapiens | HVEM shRNA #2 | GAGCUGACGGGCACAGUGUGU | 8 |

Each of the prepared shRNAs was introduced into the mesenchymal subtype cells (U3024MG cells, U3031MG cells or U3054MG cells) cultured under the conditions described in Example 1 (1). Next, the HVEM expression in the GBM cells (U3024MG cells, U3031MG cells or U3054MG cells) into which each shRNA was introduced was analyzed by quantitative RT-PCR. Specifically, the primers used were SEQ ID NOs: 1 to 4 shown in Table 1, and RT-PCR was performed according to the method described in Example 2 (2).

(2) Inhibition of HVEM by Antibody

An antibody against human HVEM (MAB356, manufactured by R & D Systems, Inc.) or a mouse IgG1 antibody (MAB002, manufactured by R & D Systems, Inc.) as a control was used to suppress the function of HVEM on the surface of GBM cells (U3024MG cells, U3031MG cells or U3054MG cells), for investigating the proliferation of the GBM cells. Specifically, 10 µg/mL of the human HVEM antibody or mouse IgG1 isotype control antibody was added to a culture solution, and the GBM cells were treated with the anti-human HVEM antibody or control antibody.

(3) In Vitro Cell Proliferation Assay

For the cells prepared in the above items (1) and (2), an in vitro cell proliferation assay was performed according to the method described in Example 1 (3).

(4) Sphere Formation Assay

For the cells prepared in the above item (1), a sphere formation assay was performed according to the method described in Example 1 (4).

(5) Results

Figure 4:
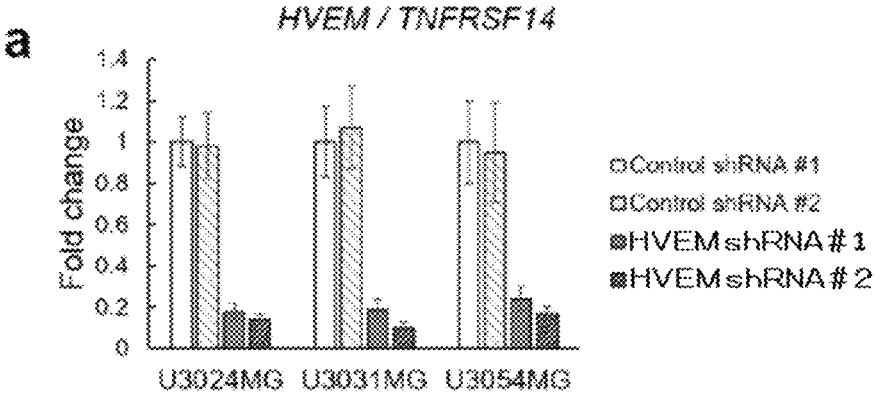
FIG. 4a is a diagram showing quantitative RT-PCR analysis of HVEM at the time of HVEM knockdown by lentivirus-mediated shRNAs in the mesenchymal subtype cells (U3024MG, U3031MG and U3054MG) in Example 4. Data is indicated as mean±SD (n=3 biological replicates).
FIG. 4b is a diagram showing that, in Example 4, blockade of HVEM inhibits proliferation of the mesenchymal subtype cells in cell culture. Growth curves of the mesenchymal subtype cells expressing HVEM shRNAs or control shRNAs. Data is indicated as mean±SD (n=4 biological replicates for a cell proliferation assay; P<0.01, *P<0.001; two-tailed unpaired Student's t-test with Bonferroni's correction for the cell proliferation assay).
FIG. 4c is a diagram showing that, in Example 4, blockade of HVEM inhibits neurosphere formation of the mesenchymal subtype cells in cell culture. Sphere formation of the mesenchymal subtype cells expressing HVEM shRNAs or control shRNAs. Data is indicated as mean±SD (n=3 biological replicates for a sphere formation assay; P<0.01, *P<0.001; two-way analysis of variance with Bonferroni's correction for the sphere formation assay).
FIG. 4d is a diagram showing an influence of an anti-human HVEM antibody on proliferation of the mesenchymal subtype cells in Example 4. Data is indicated as mean±SD (n=3 biological replicates; P<0.05, P<0.01, ***P<0.001; two-tailed unpaired Student's or Welch's t-test).
Figure 4:
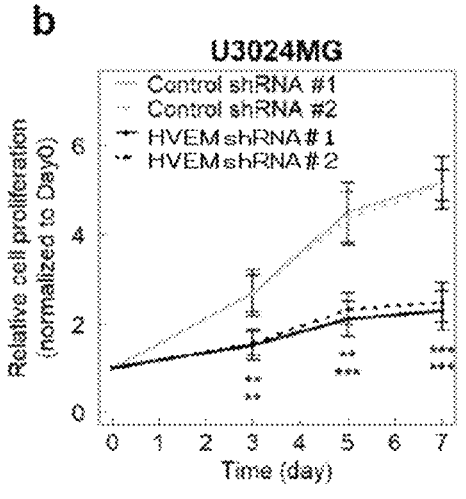
Figure 4:
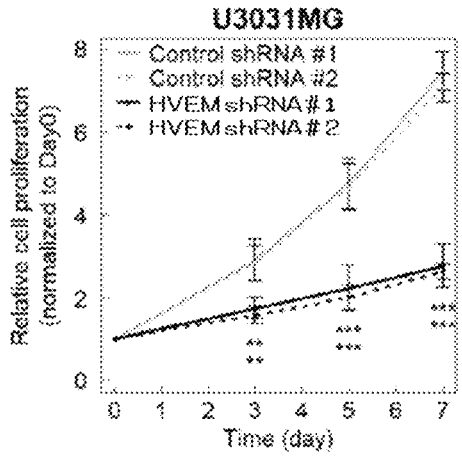
Figure 4:
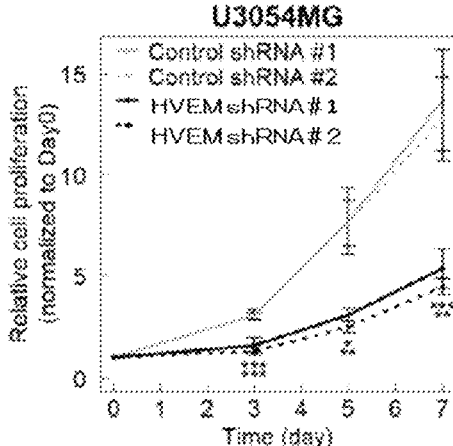
Figure 4:
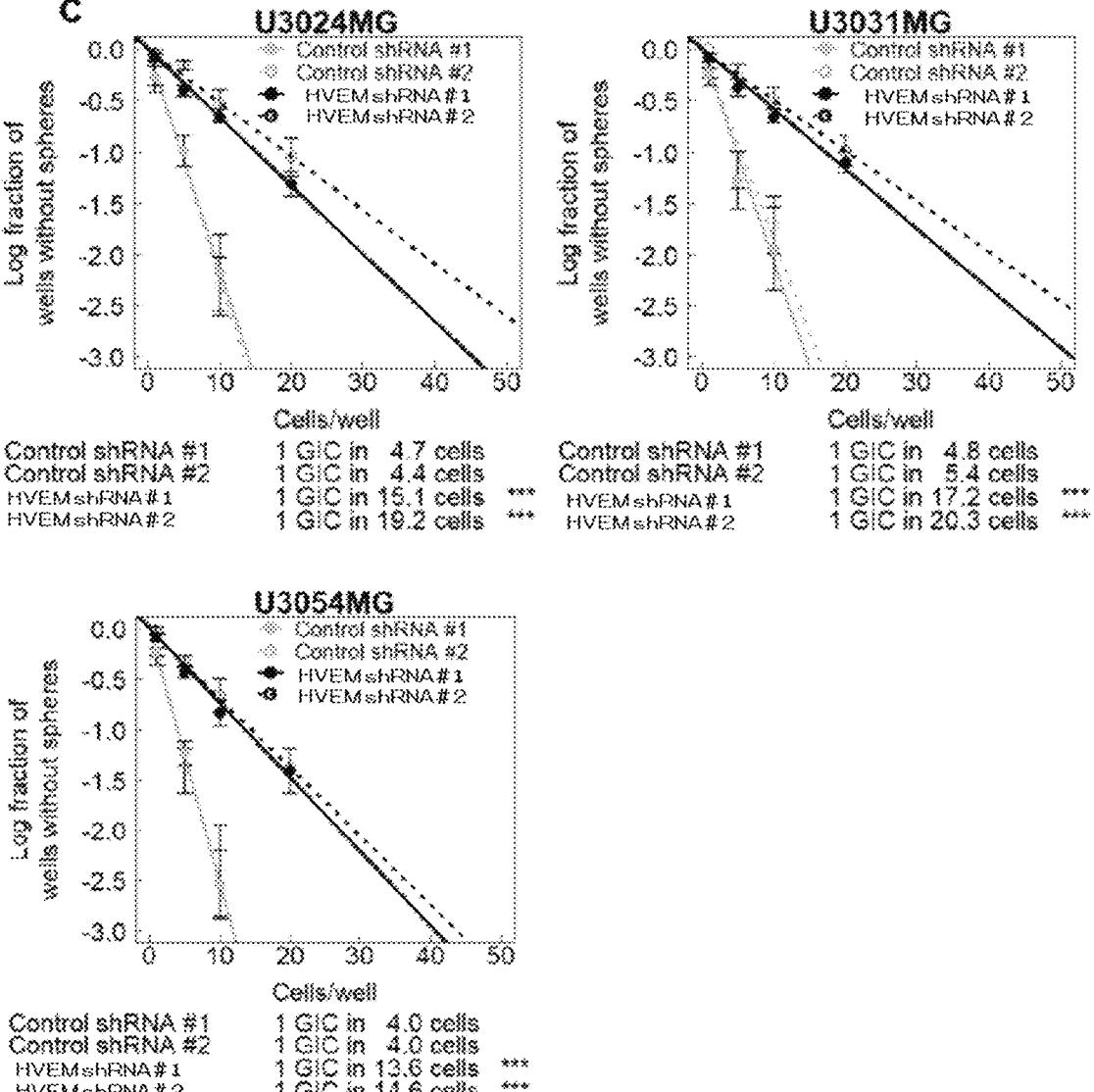
Figure 4:
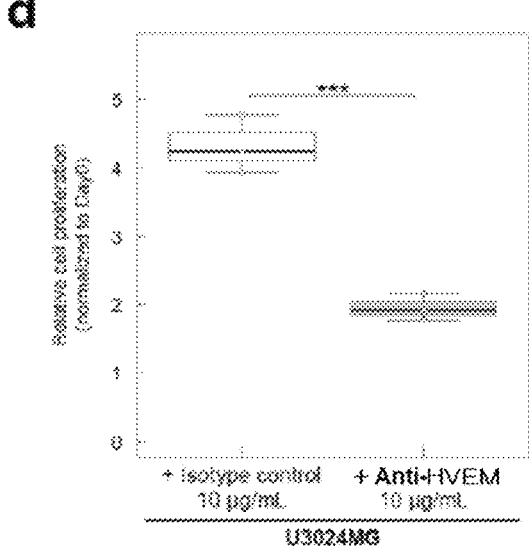
Figure 4:
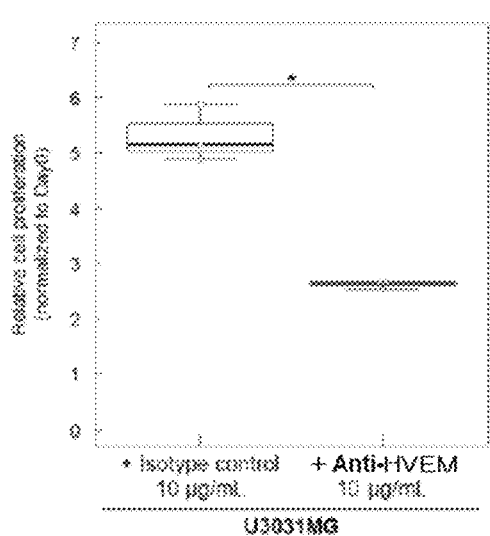
Figure 4:
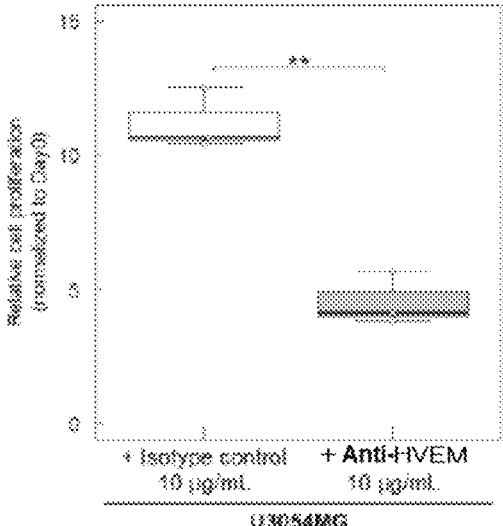

The results were as shown in FIG. 4. Knockdown of HVEM by shRNA attenuated the proliferation of all the three cell strains of the mesenchymal subtype (FIGS. 4A and 4b). In addition, the sphere formation ability of the mesenchymal subtype cells was strongly suppressed by knockdown of HVEM expression (FIG. 4c). It was also confirmed that cell proliferation was significantly attenuated in the mesenchymal subtype cultured cells treated with the anti-human HVEM antibody (FIG. 4d). It was shown that cell proliferation and sphere formation in the U3054MG cells were not inhibited by BMP-4 (see FIG. 1), but were inhibited by HVEMshRNA. From these results, it was suggested that HVEM has the effect of promoting cell proliferation of the mesenchymal subtype cells and sphere formation also in signal systems other than BMP-4.

Example 5: Suppression of In Vivo Tumor Growth of GBM Cell by Silencing of HVEM (1) Inhibition of HVEM by shRNA in GBM Cell Firefly luciferase (Luc2, manufactured by Promega Corporation, the same applies hereinafter) was introduced into the mesenchymal subtype cells (U3031MG cells or U3054MG cells) to prepare mesenchymal subtype cells expressing firefly luciferase, in the same manner as described in Example 4 (1) except that firefly luciferase Luc2 was cloned into the pENTR201 vector (manufactured by Thermo Fisher Scientific Inc.), and that recombination between the pENTR201-Luc2 and CS-CMV-RfA vectors was catalyzed by LR CLONASE® (Thermo Fisher Scientific Inc.). Control shRNA #1 (SEQ ID NO: 5) or HVEMSHRNA #1 or #2 (SEQ ID NO: 7 or 8) indicated in Table 2 was introduced into the mesenchymal subtype cells according to the method described in Example 4 (1), thereby preparing mesenchymal subtype cells expressing firefly luciferase and control shRNA or HVEMshRNA.

(2) Intracranial Transplantation of GBM Cell

The tumorigenic activity of HVEM was investigated by intracranial orthotopic transplantation of the GBM cells prepared in the above item (1) into nude mice. Specifically, $1 \times 10^5$ surviving cells, in total, were transplanted 2 mm to the right of the sagittal suture from the bregma of the skull of BALB/c nu/nu and 3 mm below the surface of the skull. After intraperitoneal injection of firefly luciferin (manufactured by Promega Corporation) into mice, in vivo biolumi-nescence imaging was performed with NightOWL LB981 NC100T (manufactured by Berthold Technologies). The mice were monitored until they lost 20% or more of body weight or showed a neurological sign such as hemiparesis, according to the rules of the Animal Ethics Committee of the University of Tokyo.

(3) Results

Figure 5:
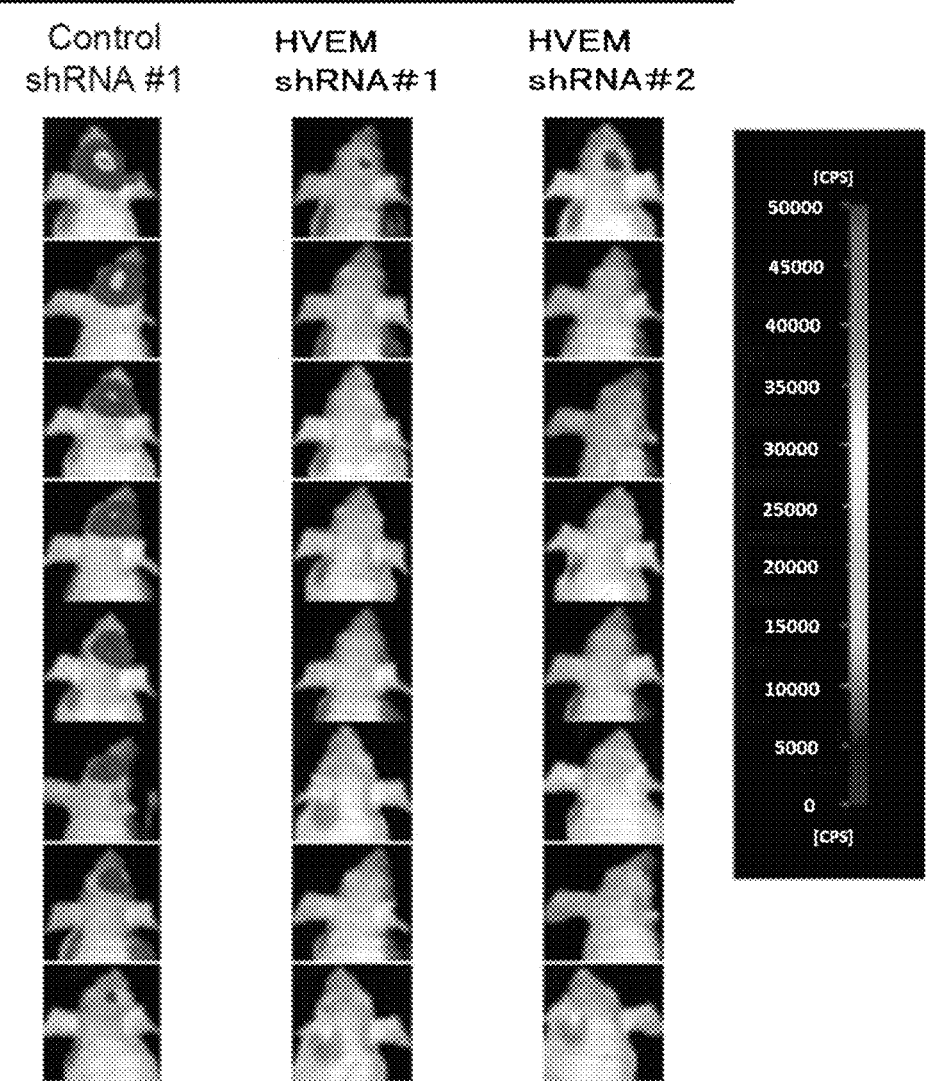
FIG. 5a is a diagram showing that, in Example 5, silencing of HVEM attenuates the in vivo tumorigenic activity of the mesenchymal subtype cells. Images of the mesenchymal subtype cells expressing shRNAs and firefly luciferase in the mouse skull by an in vivo bioluminescence imaging system. The luminescence intensity of the tumor composed of firefly luciferase-expressing GBM cells orthotopically transplanted into the mouse head was observed 15 weeks after the transplantation. For U3031 MG cells, eight mice each were used in the experiment. A region shown in black in the mouse head is the tumor composed of the GBM cells, Follow copy and a white region in the center thereof is a portion with a higher emission intensity (count per second; cps) (about 8,000 to 38,000 cps) than that of the peripheral part.
FIG. 5b is a diagram showing that, in Example 5, silencing of HVEM attenuates the in vivo tumorigenic activity of the mesenchymal subtype cells. Survival curves of mice with a tumor derived from shRNA-expressing mesenchymal subtype cells (n=8 in each group for U3031MG, n=4 in each group for U3054MG; *P<0.05, ***P<0.001; two-tailed logrank test with Bonferroni's correction).
Figure 5:
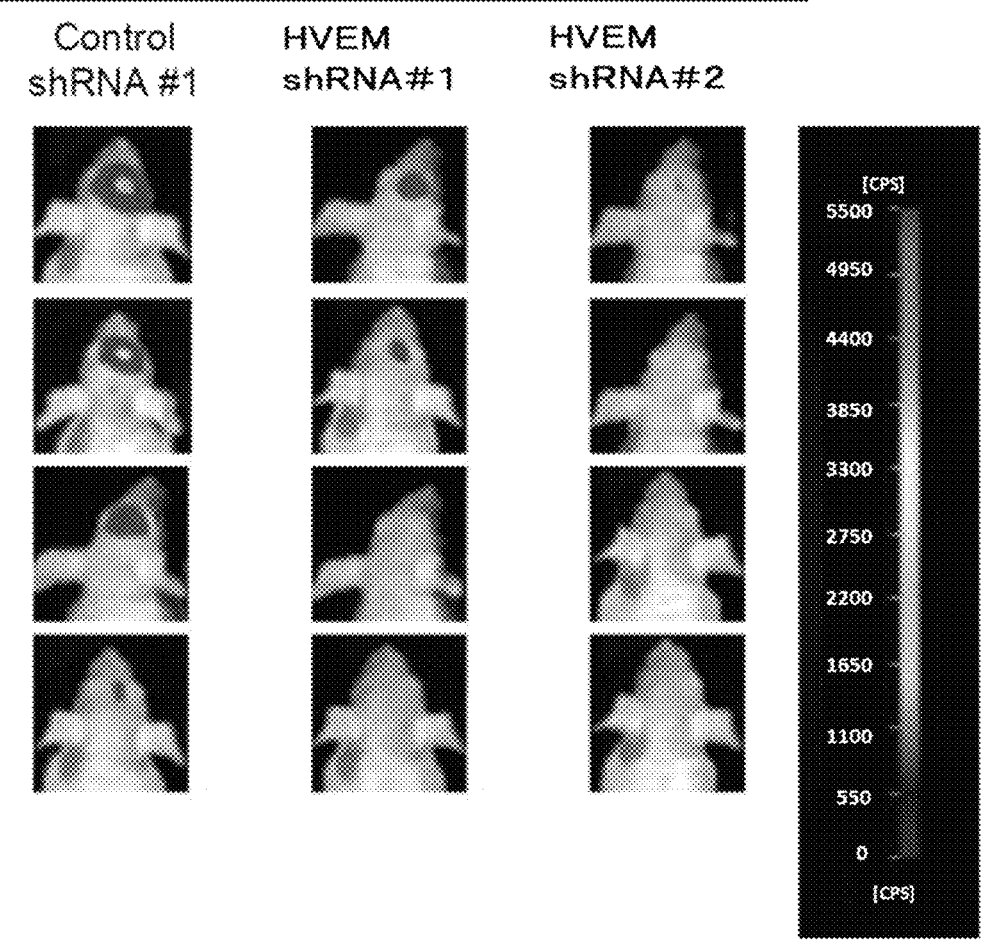
Figure 5:
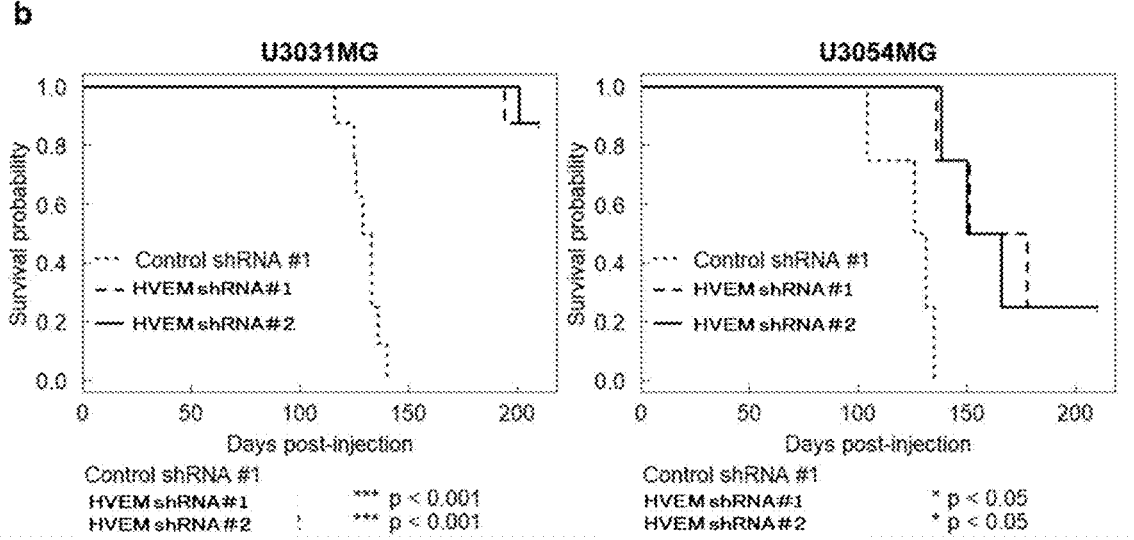

The results were as shown in FIG. 5. In vivo biolumi-nescence imaging showed that both of U3031MG and U3054MG cells treated with untargeted control shRNA #1 formed a tumor after transplantation of the cells. In contrast, the cells treated with HVEMshRNA #1 or #2 formed a smaller tumor than that of the control cells, and biolumi-nescent signals were reduced or not detected in the mice 15 weeks after the cell transplantation (FIG. 5a). It was also confirmed that silencing of the HVEM expression in the GBM cells prolonged the survival time of the mice, as compared with the mice having the GBM cells expressing the control shRNA (FIG. 5b).

Example 6: Promotion of GBM Cell Proliferation, Neurosphere Formation and In Vivo Tumor Growth by Overexpression of HVEM (1) In Vitro Overexpression of HVEM Enhanced green fluorescent protein (EGFP) or HVEM was expressed in GBM non-mesenchymal subtype cells (U3047MG, U3085MG and U3017MG cells) cultured under the conditions described in Example 1 (1) in the same manner as described in Example 4 (1), except that EGFP, HVEM or Luc2 cDNA was cloned into the pENTR201 vector (manufactured by Thermo Fisher Scientific Inc.), and that recombination between the pENTR201 and CSII-EF-RfA or CS-CMV-RfA vectors was catalyzed by LR CLO-NASE® (manufactured by Thermo Fisher Scientific Inc.).

(2) In Vitro Cell Proliferation Assay

For the cells prepared in the above item (1), an in vitro cell proliferation assay was performed according to the method described in Example 1 (3).

(3) Sphere Formation Assay

For the cells prepared in the above item (1), a sphere formation assay was performed according to the method described in Example 1 (4).

(4) In Vivo Overexpression of HVEM

The in vivo tumorigenic activity was examined for the EGFP- or HVEM-overexpressing U3047MG cells prepared in the above item (1). Specifically, the U3047MG cells were orthotopically transplanted into the skull of nude mice (BALB/c nu/nu) according to the method described in Example 5 (2), and in vivo bioluminescence imaging was performed.

(5) Results

Figure 6:
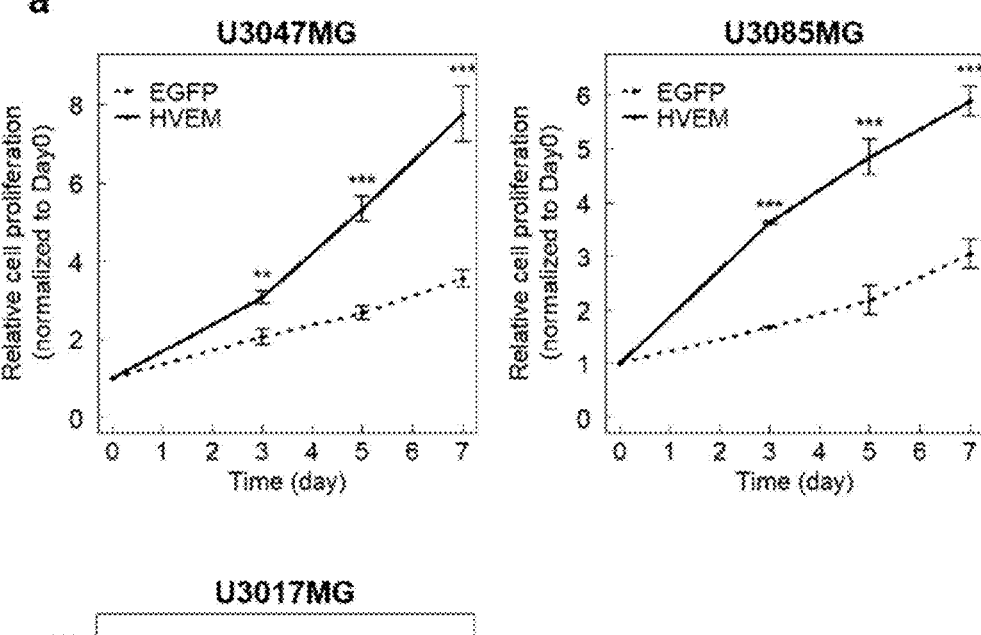
FIG. 6a is a diagram showing that ectopic HVEM promotes proliferation of non-mesenchymal subtype cells in Example 6. Growth curves of the non-mesenchymal subtype cells expressing HVEM or EGFP (control). Data is indicated as mean±SD (n=3 biological replicates; P<0.01, *P<0.001; two-tailed unpaired Student's t-test).
FIG. 6b is a diagram showing that ectopic HVEM promotes neurosphere formation of the non-mesenchymal subtype cells in Example 6. Sphere formation of the non-mesenchymal subtype cells expressing HVEM or EGFP (control). Data is indicated as mean±SD (n=3 biological replicates; P<0.01, *P<0.001; two-tailed unpaired Student's t-test).
Figure 6:
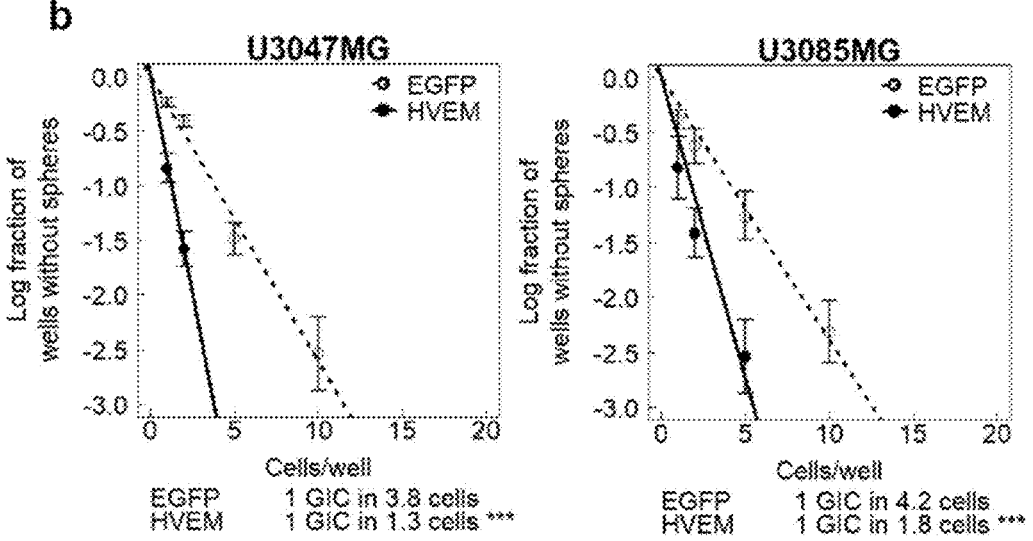
Figure 6:
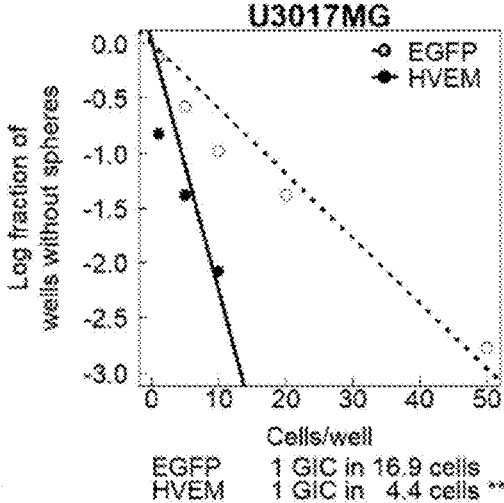
Figure 7:
FIG. 7a is a diagram showing that ectopic HVEM enhances the in vivo tumorigenic activity of the non-mesenchymal subtype cells in Example 6. Images of the non-mesenchymal subtype cells (U3047MG) expressing EGFP or HVEM proliferated in the mouse skull by an in vivo bioluminescence imaging system. The luminescence intensity of the tumor composed of the non-mesenchymal subtype cells expressing firefly luciferase orthotopically transplanted into the mouse head and EGFP or HVEM was observed 7 weeks after the transplantation. Six mice each were used in the experiment. A region shown in black in the mouse head is the tumor composed of the GBM cells, a white region in the inside thereof is a portion (about 10,000 to 40,000 cps) with a higher emission intensity than that of the peripheral part, and a region further found in black in the center thereof is a portion with a further higher emission intensity (about 40,000 cps or more).
FIG. 7b shows survival curves of mice with a tumor derived from EGFP- or HVEM-expressing non-mesenchymal subtype cells (U3047MG) in Example 6 (n=6 mice per group; ***P<0.001; two-tailed logrank test).
Figure 7:
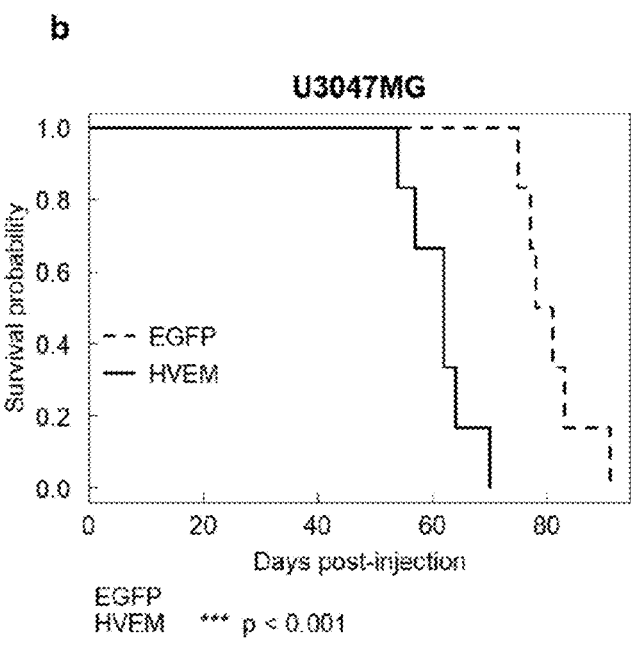

The results were as shown in FIGS. 6 and 7. The U3047MG, U3085MG and U3017MG cells belong to the proneural, neural and classical subtypes of GBM cells, respectively, and have a lower HVEM expression level than that of the mesenchymal subtype cells (see FIG. 3d). Over-expression of HVEM in these cells increased cell prolifera-tion as compared with the control cells into which EGFP was introduced (FIG. 6a). Furthermore, the sphere formation ability was enhanced by overexpression of HVEM (FIG. 6b). These findings confirmed the role of HVEM in main-taining the stem cell-like properties of glioblastoma cells. In addition, in FIG. 7, the bioluminescent signal varied between the respective mice, but HVEM promoted tumor growth in vivo (FIG. 7a), and the mice transplanted with the U3047MG cells expressing HVEM were compared to have a short survival time as compared with the control mice (FIG. 7b).

Example 7: Suppression of Tumorigenicity of Murine Glioma Cells by HVEM Inhibition (1) HVEM Expression and Serum The function of HVEM was analyzed using a murine glioma cell strain GL261 (manufactured by PerkinElmer, Inc.). GL261 cells were cultured in a DMEM (manufactured by Thermo Fisher Scientific Inc.) medium added with 10% fetal bovine serum (fetal bovine serum-containing differen-tiation medium) or the serum-free stem cell medium described in Example 1 (1). Quantitative RT-PCR was performed using the primers indicated in Table 3 according to the method described in Example 2 (2).

[Table 3]

TABLE 3

| Primer set used in quantitative RT-PCR | | | | |
|---|---|---|---|---|
| Species | Target gene | Forward/ reverse | Sequence (5' → 3') | SEQ ID NO: |
| Mus musculus | GAPDH | Forward | TGCAGTGGCAAAGTGGAGATT | 9 |
| Mus musculus | GAPDH | Reverse | TGCCGTTGAATTTGCCGT | 10 |
| Mus musculus | HVEM | Forward | AATGGAACCTCTCCCAGGAT | 11 |
| Mus musculus | HVEM | Reverse | AGGAAGACACAAGGCACCA | 12 |

Figure 8:
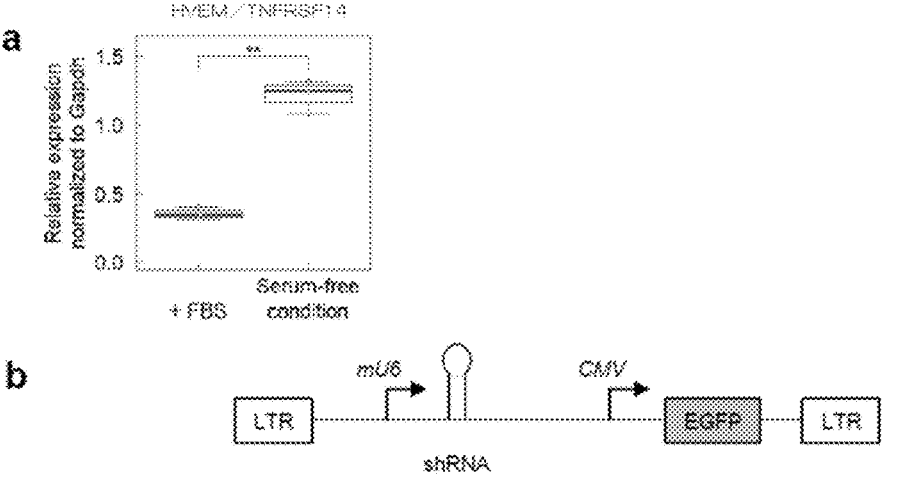
FIGS. 8a and 8b are diagrams showing that HVEM is required for in vivo progression of murine glioma cells in Example 7. (a) An expression level of HVEM in a murine glioma GL261 cell strain. GL261 cells were cultured in a fetal bovine serum-containing differentiation medium or a serum-free stem cell medium. Data is indicated as mean±SD (n=3 biological replicates; ***P<0.001; two-tailed unpaired Student's t-test). (b) Intracranial proliferation of GL261 cells expressing HVEM or control shRNAs in the brain of C57BL/6J mice. EGFP and shRNA were lentivirally transduced into the GL261 cells at the same time. Mouse brain tissue was subjected to hematoxylin and eosin (H & E) staining or bioluminescence imaging for EGFP.
FIG. 8c is a diagram showing that HVEM is required for in vivo progression of murine glioma cells in Example 7. The upper figure shows brain tissue hematoxylin and eosin-stained 25 days after the intracranial orthotopic transplantation of the murine glioma cells GL261. The lower figure shows survival curves of C57BL/6J mice with a GL261-derived tumor in an anti-HVEM antibody-administered group and a control (n=6 mice per group; **P<0.01; to-sided logrank test). Five days after the intracranial injection of the GL261 cells, an anti-mouse HVEM antibody or isotype control antibody was injected intraperitoneally into the mice every 5 days.
Figure 8:
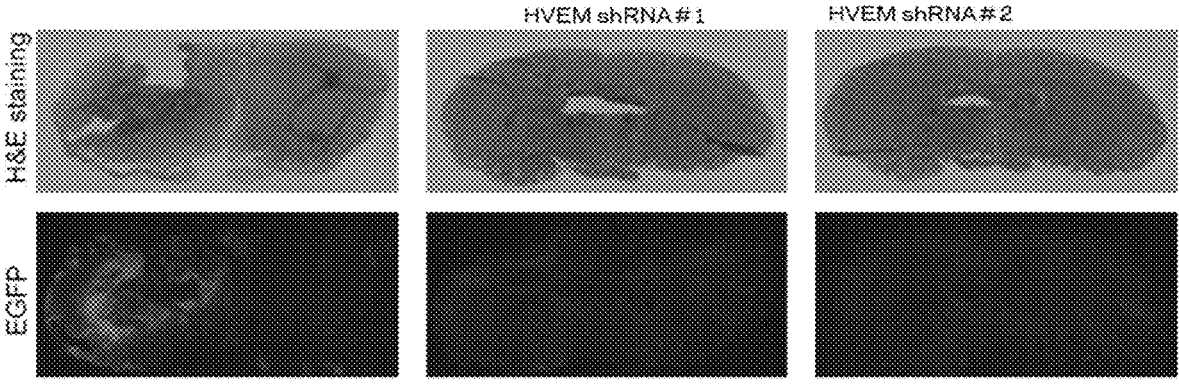
Figure 8:
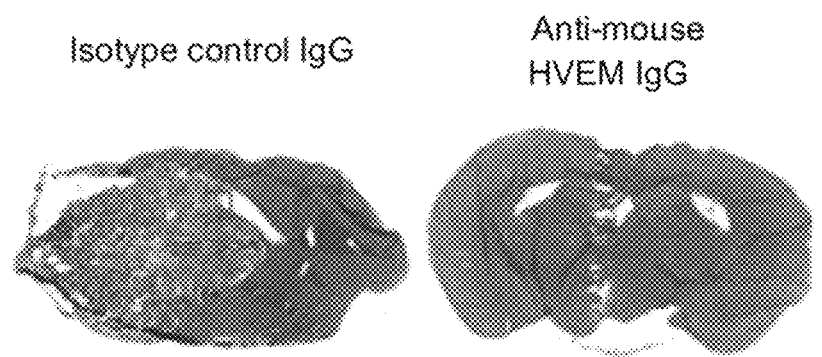
Figure 8:
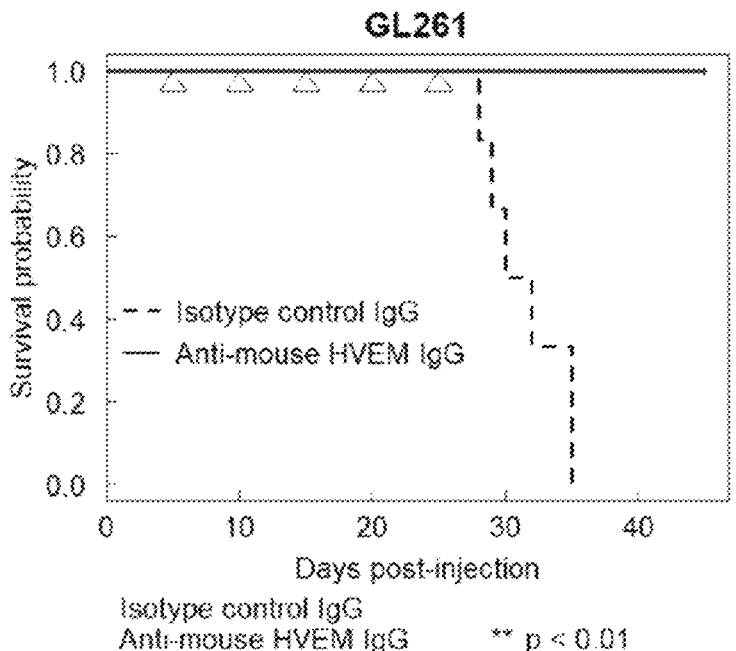

The results were as shown in FIG. 8a. Expression of HVEM was detected when the cells were proliferated in the serum-free medium, but decreased in the presence of serum. From these results, it was confirmed that the GL261 cells differentiate in the presence of serum, and that the HVEM expression decreases.

(2) Tumorigenic Activity of HVEM

A vector having a DNA sequence and an EGFP sequence encoding HVEMshRNA #1 or #2 (SEQ ID NO: 13 or 14) or control shRNA #1 (SEQ ID NO: 5) indicated in Table 4 was introduced into GL261 cells according to the method described in Example 4 (1). By orthotopic transplantation of the GL261 cells into the skull of C57BL/6J mice, the tumorigenic activity of HVEM in the GL261 cells after suppressing the expression of HVEM was examined. Specifically, 1×10$^5$ surviving cells, in total, were transplanted 2 mm to the right of the sagittal suture from the bregma of the skull and 3 mm below the surface of the skull. Mice transplanted with glioma cells were transcardially perfused with 4% paraformaldehyde. The brain tissue of the mice was cryoprotected with 10 to 20% sucrose, and tissue sections were stained with hematoxylin and eosin. The results were as shown in FIG. 8b. The GL261 cells treated with control shRNA formed a tumor after cell transplantation (EGFP signals were observed), whereas the murine glioma cells treated with HVEMshRNA did not form a tumor (FIG. 8b). From these results, it was confirmed that the tumorigenic activity of glioma cells can be suppressed by suppressing the expression of HVEM in the glioma cells.

[Table 4]

TABLE 4

| shRNA sequence | | | |
|---|---|---|---|
| Species | shRNA | Target sequence of shRNA (5' → 3') | SEQ ID NO: |
| | Control shRNA #1 | GUGGUUUACAUGUCGACUAA | 5 |
| Mus musculus | HVEM shRNA #1 | GCAACCCAGGUUACCAUGUGA | 13 |
| Mus musculus | HVEM shRNA #2 | GUGAGCAUACAGGCACAGUGU | 14 |

(3) Increase of Survival Probability by Anti-HVEM Antibody

Through orthotopic transplantation of GL261 cells (BW134246V, manufactured by PerkinElmer, Inc.) expressing firefly luciferase (RedFLuc) into the skull of C57BL/6J mice, the function of HVEM was investigated in vivo using an anti-HVEM antibody. Specifically, 5 days after intracranial transplantation of the GL261 cells according to the method described in the above item (2), the mice were equally divided into two groups (an anti-mouse HVEM antibody group and an isotype control IgG1 group) based on the luminescence intensity of firefly luciferase, based on in vivo bioluminescence imaging. Then, 5 days after intracranial transplantation of the GL261 cells, 7.5 mg/kg of an anti-mouse HVEM hamster monoclonal IgG antibody (prepared according to LBH1, Xu Y et al., Blood, 109:4097-4104 (2007)) or a hamster isotype IgG antibody as a control (I-140, manufactured by Leinco Technologies, Inc.) was intraperitoneally injected, and the injection was performed 5 times, in total, every five days. The results were as shown in FIG. 8c. Hematoxylin/eosin staining in brain tissue confirmed that a tumor was formed in the control group 25 days after transplantation of the GL261 cells, but that tumor formation was suppressed in the group administered with the anti-mouse HVEM antibody. All mice in the control antibody-treated group died within 35 days, while all the mice in the anti-mouse HVEM antibody-treated group survived longer than 45 days. From these results, it was confirmed that suppression of the function of HVEM in the glioma cells can suppress the tumorigenic activity of the glioma cells and can also prolong the survival time.

Figure 9:
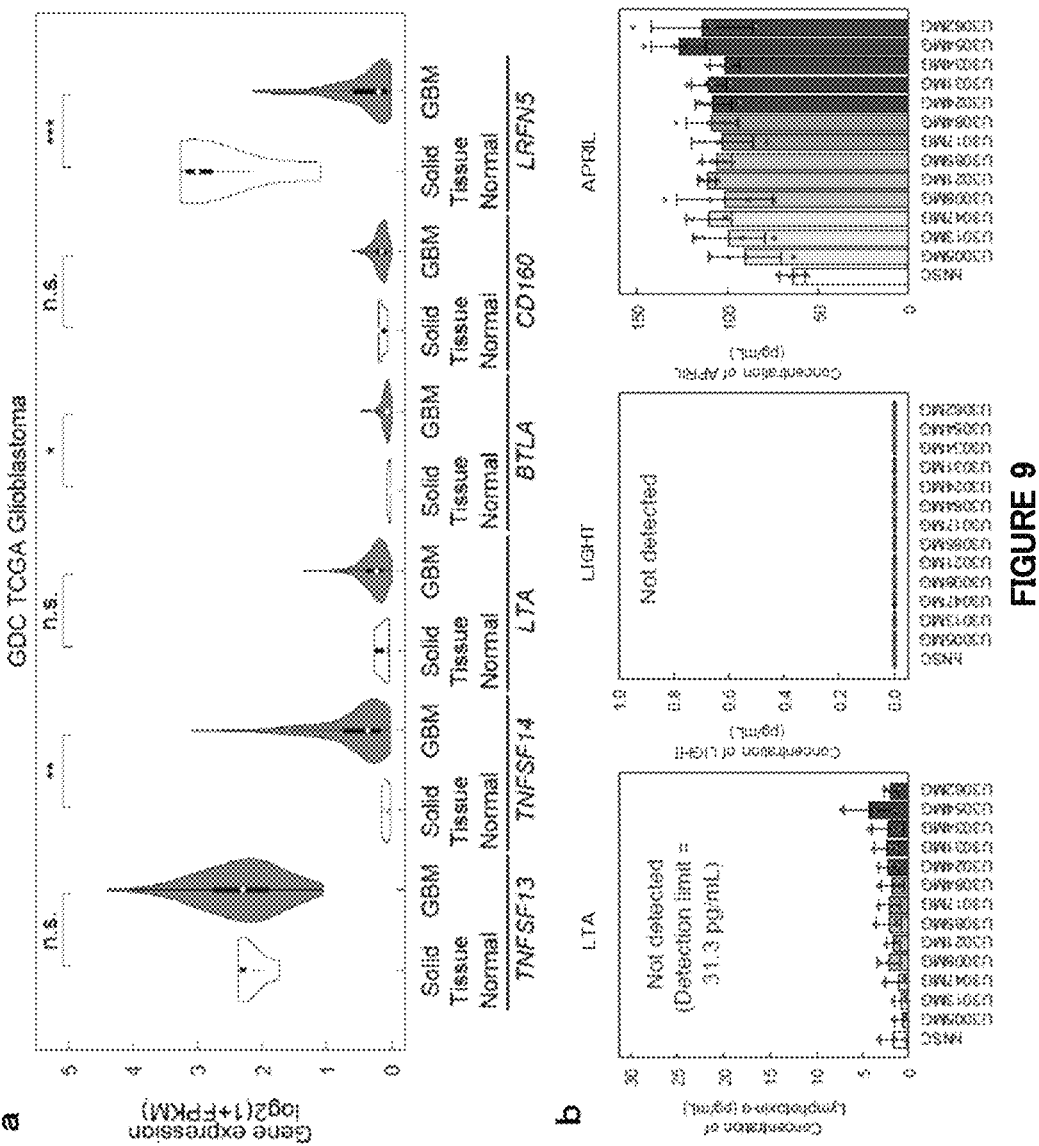
FIGS. 9a and 9b are diagrams showing expression of ligands for HVEM in a brain tumor in Example 8. (a) Expression levels of HVEM ligands and APRIL in normal brain tissue and a brain tumor in the TCGA dataset (* P<0.05, P<0.01, *P<0.001, ns: not significant (P>0.05); two-tailed Kruskal-Wallis test). (b) Expression levels of LTA, LIGHT and APRIL in hNSC and GBM cells from HGCC resources as measured by sandwich ELISA.

Example 8 Expression of Ligand for HVEM in GBM (1) Expression of Ligand for HVEM in GBM To investigate the function of a ligand for HVEM in brain tumors, the expression levels of mRNAs of APRIL and known ligands (LIGHT, LTA, BTLA, CD160 and SALM5) for HVEM were analyzed using the GDC TCGA dataset. The results were as shown in FIG. 9a. APRIL was observed to be highly expressed in normal brain tissue and GBM as compared with the known ligands for HVEM.

(2) Expression of Ligand for HVEM in GBM Subtype

The amounts of APRIL and the known ligands for HVEM (LTA and LIGHT) in culture supernatants of 13 different GBM cell strains and H9 hESC-derived human neural stem cells (hNSCs) were measured by sandwich ELISA. Specifically, human APRIL, LTA and LIGHT in the cell supernatants were quantified by immunoassay using the following reagents: human APRIL/TNFSFT3 DUOSET® ELISA (DY884B, R & D Systems, Inc.), human Lymphotoxin-alpha/TNF-beta DUOSET® ELISA (DY211, R & D Systems, Inc.), human LIGHT/TNSF14 QUANTIKINE® ELISA Kit (DLIT00, R & D Systems, Inc.), and Auxiliary Reagent Kit 2 (DY008, R & D Systems, Inc.). The absorbances at 450 nm and 570 nm were measured with a Model 680 microplate reader (Bio-Rad Laboratories, Inc.) or Enspire (PerkinElmer, Inc.). The results were as shown in FIG. 9b. The concentrations of LTA and LIGHT in the culture supernatants were not higher than the detection sensitivity. On the other hand, it was confirmed that APRIL was present in human neural stem cell (hNSC) and all the 13 types of GBM at a concentration of 50 μg/mL or more, and that the expression amount of APRIL was higher in GBM than in normal brain tissue.

From these results, it was clarified that none of the known ligands for HVEM were highly expressed in GBM, and that APRIL, which had not been reported as a ligand for HVEM, was highly expressed. APRIL is a ligand of the TNF superfamily, and BCMA/TNFRSF17 and TACI/TNFRSF13B are known as receptors for APRIL. It had not been reported so far that APRIL binds to HVEM and transduces signals.

Example 9: Suppression of Proliferation of GBM Cell and Neurosphere Formation by Inhibition of APRIL (1) Inhibition of APRIL by shRNA Short hairpin RNAs (shRNAs) were used to inhibit APRIL according to the method described in Example 4 (1), except that DNA sequences encoding the shRNAs indicated in Table 5, mesenchymal subtype cells (U3054MG cells) and the primers for APRIL indicated in Table 6 were used (FIG. 10a).

[Table 5]

TABLE 5

| shRNA sequence | | | |
|---|---|---|---|
| Species | shRNA | Target sequence of shRNA (5' → 3') | SEQ ID NO: |
| Homo sapiens | Control shRNA #1 | GUGGUUUACAUGUCGACUAA | 5 |

TABLE 5-continued shRNA sequence

| Species | shRNA | Target sequence of shRNA (5' → 3') | SEQ ID NO: |
|---|---|---|---|
| Homo sapiens | Control shRNA #2 | AUGGUUUACAUGUUGUGUGA | 6 |
| Homo sapiens | APRIL shRNA #1 | GAGACUCUAUUCCGAUGUAUA | 15 |
| Homo sapiens | APRIL shRNA #2 | GGCAAGGGCGAAACUUAACCU | 16 |

[Table 6]

TABLE 6

Primer set used in quantitative RT-PCR

| Species | Target gene | Forward/ reverse | Sequence (5' → 3') | SEQ ID NO: |
|---|---|---|---|---|
| Homo sapiens | GAPDH | Forward | GAAGGTGAAGGTCGGAGTC | 1 |
| Homo sapiens | GAPDH | Reverse | GAAGATGGTGATGGGATTTC | 2 |
| Homo sapiens | APRIL | Forward | TATAGCGCAGGTGTCTTCCA | 17 |
| Homo sapiens | APRIL | Reverse | ACAGTTTCACAAACCCCAGGA | 18 |

(2) Inhibition of APRIL by Antibody

The proliferation of GBM cells by suppressing the function of APRIL on the surface of the GBM cells was investigated according to the description of Example 4 (2), except that an antibody against human APRIL (anti-human APRIL/TNFSF13, MAB5860, manufactured by R & D Systems, Inc., the same applies hereinafter) was used (FIG. 10d). Except that 10 μg/mL of the antibody against human APRIL and non-mesenchymal subtype GBM cells (U3047MG) were used, the proliferation of the non-mesenchymal subtype cells by suppressing the function of APRIL on the surface of the non-mesenchymal subtype cells was investigated according to the description of Example 4 (2) (FIG. 10e).

(3) In Vitro Cell Proliferation Assay

For the cells prepared in the above items (1) and (2), an in vitro cell proliferation assay was performed according to the method described in Example 1 (3) (FIG. 10b, FIG. 10d, and FIG. 10e).

(4) Sphere Formation Assay

For the cells prepared in the above item (1), a sphere formation assay was performed according to the method described in Example 1 (4) (FIG. 10c).

(5) Expression of Receptor for APRIL in GBM

In order to investigate the functions of ligands for HVEM in brain tumors, the expression levels of mRNAs, in normal brain tissue and GBM, of HVEM and known receptors for APRIL (BCMA/TNFRSF17 and TACI/TNFRSF13B) were analyzed using the GDC TCGA dataset (FIG. 10f).

(6) Results

Figure 10:
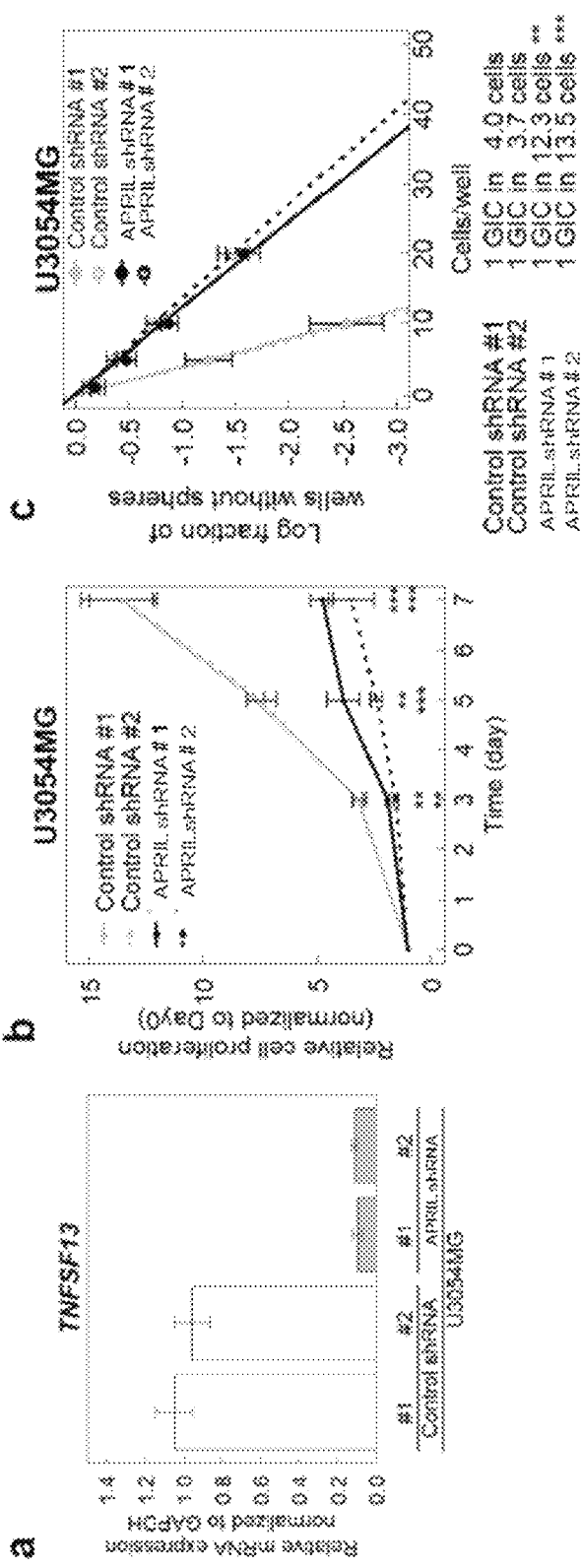
FIGS. 10a, b and c are diagrams showing an influence of APRIL knockdown by shRNAs in Example 9. (a) A diagram showing quantitative RT-PCR analysis of APRIL at the time of APRIL knockdown by lentivirus-mediated shRNAs in the mesenchymal subtype cells (U3054MG). Data is indicated as mean±SD (n=3 biological replicates). (b) A diagram showing that blockade of APRIL inhibits proliferation of the mesenchymal subtype cells in cell culture. Growth curves of the mesenchymal subtype cells expressing APRIL shRNAs or control shRNAs. Data is indicated as mean±SD (n=3 biological replicates for a cell proliferation assay; P<0.01, *P<0.001; two-tailed unpaired Student's t-test). (c) A diagram showing that blockade of APRIL inhibits neurosphere formation of the mesenchymal subtype cells in cell culture. Sphere formation of the mesenchymal subtype cells expressing APRIL shRNAs or control shRNAs. Data is indicated as mean±SD (n=3 biological replicates for a sphere formation assay; P<0.01, *P<0.001; two-tailed unpaired Student's t-test).
FIGS. 10d and e are diagrams showing an influence of APRIL inhibition in Example 9. (d) A diagram showing an influence of an anti-human APRIL antibody on proliferation of the mesenchymal subtype cells. Data is indicated as mean±SD (n=3 biological replicates; P<0.01, *P<0.001; two-tailed unpaired Student's t-test). (e) A diagram showing an influence of anti-human APRIL antibodies on proliferation of the non-mesenchymal subtype cells. Data is indicated as mean±SD (n=3 biological replicates).
FIG. 10f is a diagram showing expression of receptors for APRIL in the mesenchymal subtype cells in Example 9. (a) Expression levels of known receptors for APRIL (BCMA and TACI) and HVEM in normal brain tissue and a brain tumor in the TCGA dataset (*P<0.05, P<0.01, *P<0.001, ns: not significant (P>0.05); two-tailed Kruskal-Wallis test).
Figure 10:
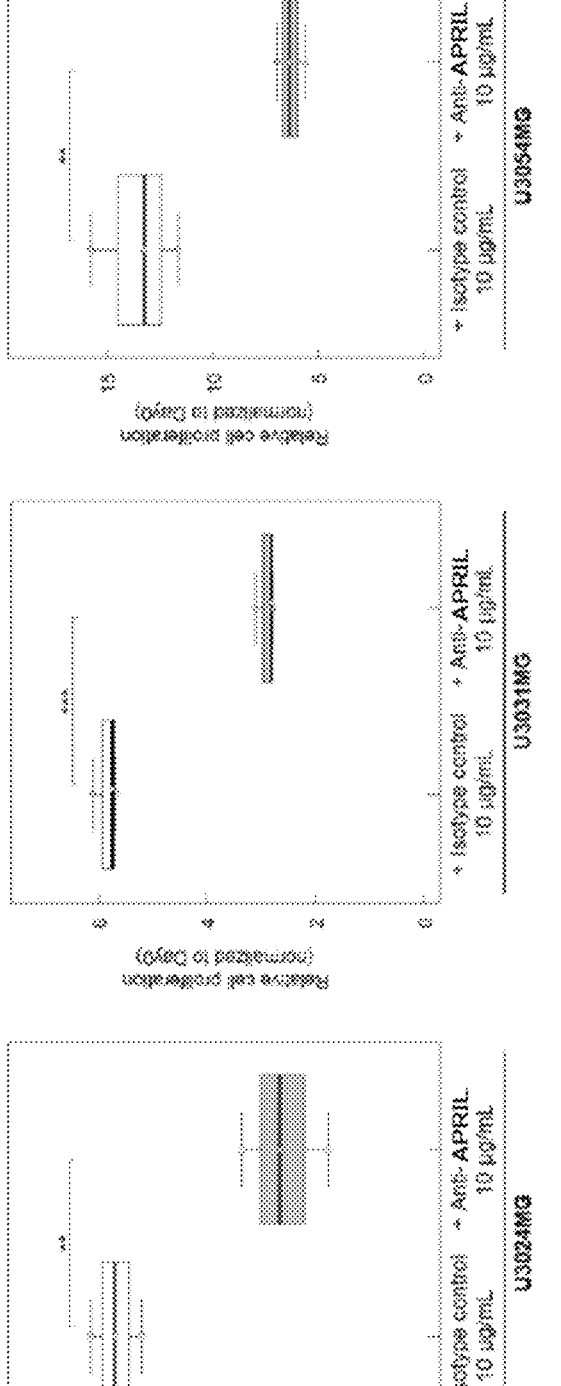
Figure 10:
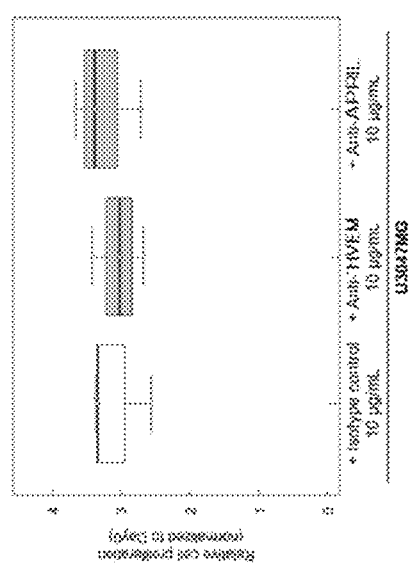
Figure 10:
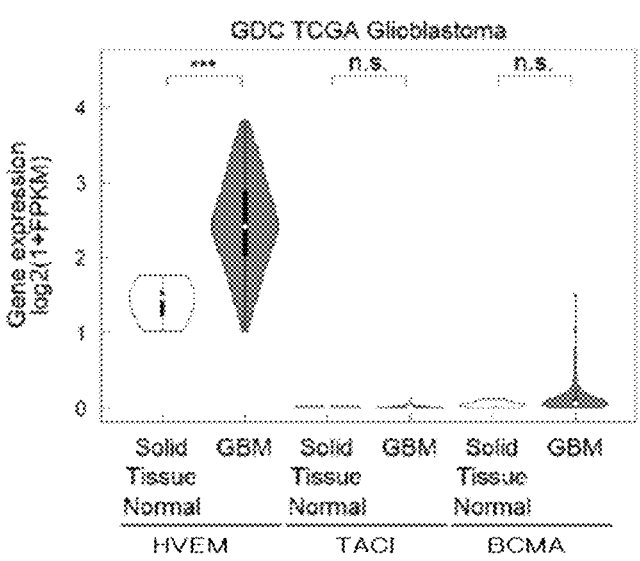

The results were as shown in FIG. 10.

Knockdown of HVEM by shRNA attenuated the proliferation of the cell strain of the mesenchymal subtype (FIG. 10b). In addition, the sphere formation ability of the mesenchymal subtype cells was strongly suppressed by knock-down of APRIL expression (FIG. 10c). It was also confirmed that cell proliferation was significantly attenuated in the mesenchymal subtype cultured cells treated with the anti-human APRIL antibody (FIG. 10d). On the other hand, cell proliferation was not attenuated in the non-mesenchymal subtype cultured cells treated with the anti-human APRIL antibody (U3047MG) (FIG. 10e). Since the U3047MG cells are a cell strain that did not express HVEM but expressed APRIL, it was suggested that expression of HVEM on brain tumor cells is necessary for suppression of cell proliferation by the human APRIL antibody. In addition, since it was confirmed that the two receptors for APRIL (BCMA and TACI) were both expressed at an extremely low level in GBM as compared with HVEM, it was suggested that APRIL was unlikely to bind to the known receptors for APRIL and to act in GBM. These results suggested that the expression of HVEM is necessary for the cell proliferation ability and sphere formation ability of APRIL in GBM.

Effect of APRIL as Ligand for HVEM (1) Identification of Ligand for HVEM pCS-NF-κB-RE-minP-Luc2-CMV-hRluc in which the firefly luciferase gene (Luc2, Promega Corporation) was cloned downstream of the minimal promoter having the NF-κB responsive element and the Renilla luciferase gene (hRluc, Promega Corporation) was cloned downstream of the CMV promoter was prepared. After introduction of human-derived HVEM into HEK293T cells using LIPO-FECTAMINE® 2000 (manufactured by Thermo Fisher Scientific Inc., the same applies hereinafter), the NF-κB responsive Luc2 gene and the constantly-expressed hRluc gene were introduced (HVEM-expressing cells). On the other hand, human-derived LIGHT, APRIL and SALM5 genes were cloned into the pENTR4-CMV vector, and recombination between pENTR4-CMV and CS-RfA-EF-PuroR was catalyzed by LR CLONASE® (manufactured by Thermo Fisher Scientific Inc.). Next, LIGHT, APRIL and SALM5 were each expressed in HEK293T cells which were different from those described above using LIPOFECTAMINE® 2000 to prepare cells expressing soluble ligands (ligand-expressing cells). As control cells, cells expressing the NF-κB reporter gene but not expressing either HVEM or the ligands were prepared (Empty). The HVEM-expressing cells and the ligand-expressing cells were co-cultured, and the activity of NF-κB in the HVEM-expressing cells was evaluated using DUAL LUCIFERASE© Reporter Assay Kit (Promega Corporation, the same applies hereinafter).

(2) Effect of Commercial APRIL and SALM5

The HVEM-expressing cells prepared in the above item (1) were stimulated with the recombinant APRIL (Pepro-Tech, Inc.), recombinant human IgG1 Fc (Control-Fc, R & D Systems, Inc.) or recombinant SALM5-Fc (chimeric protein with the Fc site of an immunoglobulin, R & D Systems, Inc.), and the activity of NF-κB in the HVEM-expressing cells was evaluated using DUAL LUCIFER-ASE® Reporter Assay Kit.

(3) Results

Figure 11:
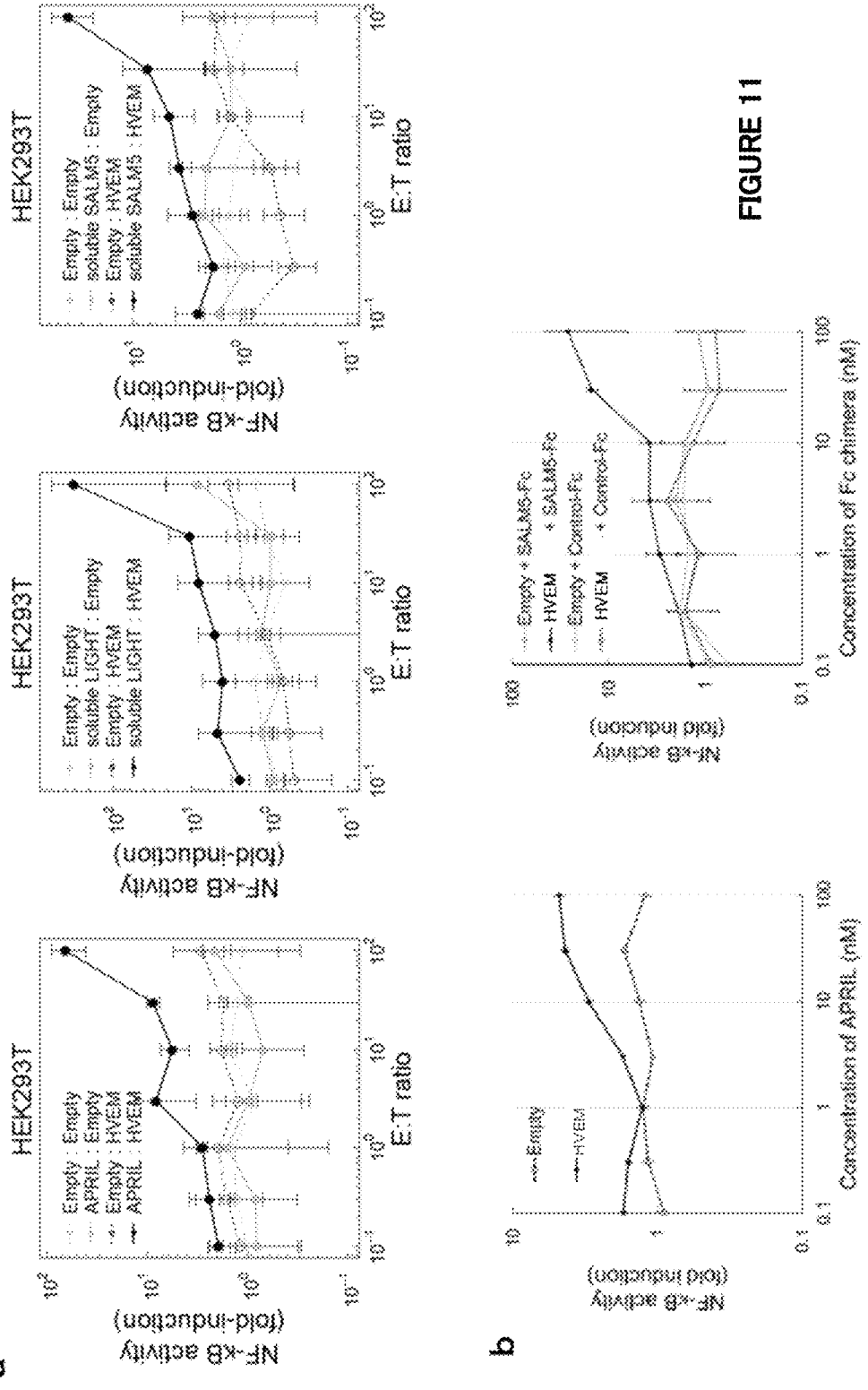
FIG. 11 is a diagram showing that APRIL transduces signals of HVEM in Example 10. (a) HEK293T cells expressing HVEM were co-cultured with HEK293T cells expressing a soluble ligand (APRIL, LIGHT or SALM5). Data is shown as mean±SD for NF-κB relative activity in HEK293T cells expressing HVEM or control vectors. (b) The HEK293T cells expressing HVEM or control vectors were stimulated by APRIL or SALM5-Fc chimera. Data is shown as mean±SD for the NF-κB relative activity.

The results were as shown in FIG. 11. Like LIGHT and SALM5 as the ligands for HVEM, APRIL was also shown to transduce signals and to activate NF-κB signals in the HVEM-expressing cells (FIG. 11a). APRIL was shown to transduce signals and to activate NF-κB signals in the HVEM-expressing HEK293T cells at a concentration of 10 to 30 nM or more, like SALM5-Fc (FIG. 11b). These results indicate that APRIL, which had not been reported so far as a ligand for HVEM, acts as a ligand for HVEM, like the known ligands for HVEM (LIGHT and SALM5). APRIL was shown to act at a concentration equivalent to that of SALM5.

Example 11: Effect of Knockout Using CRISPR/Cas9 of HVEM Gene (1) CRISPR/Cas9 System LentiCRISPR v2 vectors encoding the gRNAs, as indicated in Table 8, targeting the DNA sequences indicated in Table 7 were prepared, and hCas9 and each gRNA were introduced into mesenchymal subtype cells (U3054MG cells) or murine glioma cell strain GL261 (PerkinElmer, Inc.) using LIPOFECTAMINE® 2000. Each cell was cloned by the limiting dilution method. The gRNA sequences were selected by free software.

[Table 7]

TABLE 7

Target sequence of CRISPR/Cas9

| Species | Target gene | gRNA | Sequence (5' → 3') | SEQ ID NO: |
|---|---|---|---|---|
| | Control | Control gRNA | GTATTACTGATATTGGTGGG<u>N</u><u>GG</u> | 19 |
| Homo sapiens | TNFRSF14 | TNFRSF14 gRNA #1 | AGCAGTTCCGGCTCGCGCGC <u>AGG</u> | 20 |
| Homo sapiens | TNFRSF14 | TNFRSF14 gRNA #2 | CCCTCCGGACGTCACCACGG <u>TGG</u> | 21 |
| Mus musculus | Tnfrsf14 | Tnfrsf14 gRNA #1 | TGCGCTGCAGCAAGTTCAAA <u>AGG</u> | 22 |
| Mus musculus | Tnfrsf14 | Tnfrsf14 gRNA #2 | GCGGAGTCTGTGATCCAGGT <u>AGG</u> | 23 |

The underlined parts indicate PAM sequences recognized by hCas9. Since no target sequence of control gRNA theoretically exists on the human genome or the mouse genome, a general PAM sequence is indicated.

[Table 8]

TABLE 8

Base sequence of gRNA full length used in CRISPR/Cas9 system

| Species | gRNA | Sequence (5' → 3') | SEQ ID NO: |
|---|---|---|---|
| | Control gRNA | GGUAUUACUGAUAUUGGUGGGGUUUUA GAGCUAGAAAUAGCAAGUUAAAAUAAG GCUAGUCCGUUAUCAACUUGAAAAAGU GGCACCGAGUCGGUGCU | 24 |
| Homo sapiens | TNFRSF14 gRNA #1 | GAGCAGUUCCGGCUCGCGCGCGUUUUAG AGCUAGAAAUAGCAAGUUAAAAUAAGG CUAGUCCGUUAUCAACUUGAAAAAGUG GCACCGAGUCGGUGCU | 25 |
| Homo sapiens | TNFRSF14 gRNA #2 | GCCCUCCGGACGUCACCACGGGUUUUAG AGCUAGAAAUAGCAAGUUAAAAUAAGG CUAGUCCGUUAUCAACUUGAAAAAGUG GCACCGAGUCGGUGCU | 26 |
| Mus musculus | Tnfrsf14 gRNA #1 | GUGCGCUGCAGCAAGUUCAAAGUUUUA GAGCUAGAAAUAGCAAGUUAAAAUAAG GCUAGUCCGUUAUCAACUUGAAAAAGU GGCACCGAGUCGGUGCU | 27 |

TABLE 8-continued

Base sequence of gRNA full length used in CRISPR/Cas9 system

| Species | gRNA | Sequence (5' → 3') | SEQ ID NO: |
|---|---|---|---|
| Mus musculus | Tnfrsf14 gRNA #2 | GGCGGAGUCUGUGAUCCAGGUGUUUUA GAGCUAGAAAUAGCAAGUUAAAAUAAG GCUAGUCCGUUAUCAACUUGAAAAAGU GGCACCGAGUCGGUGCU | 28 |

(3) In Vitro Cell Proliferation Assay

For the cells prepared in the above item (1), an in vitro cell proliferation assay was performed according to the method described in Example 1 (3). GL261 cells were cultured in a serum-free stem cell medium according to the description of Example 1 (1).

(4) Sphere Formation Assay

For the cells prepared in the above item (1), a sphere formation assay was performed according to the method described in Example 1 (4).

(5) Results

Figure 12:
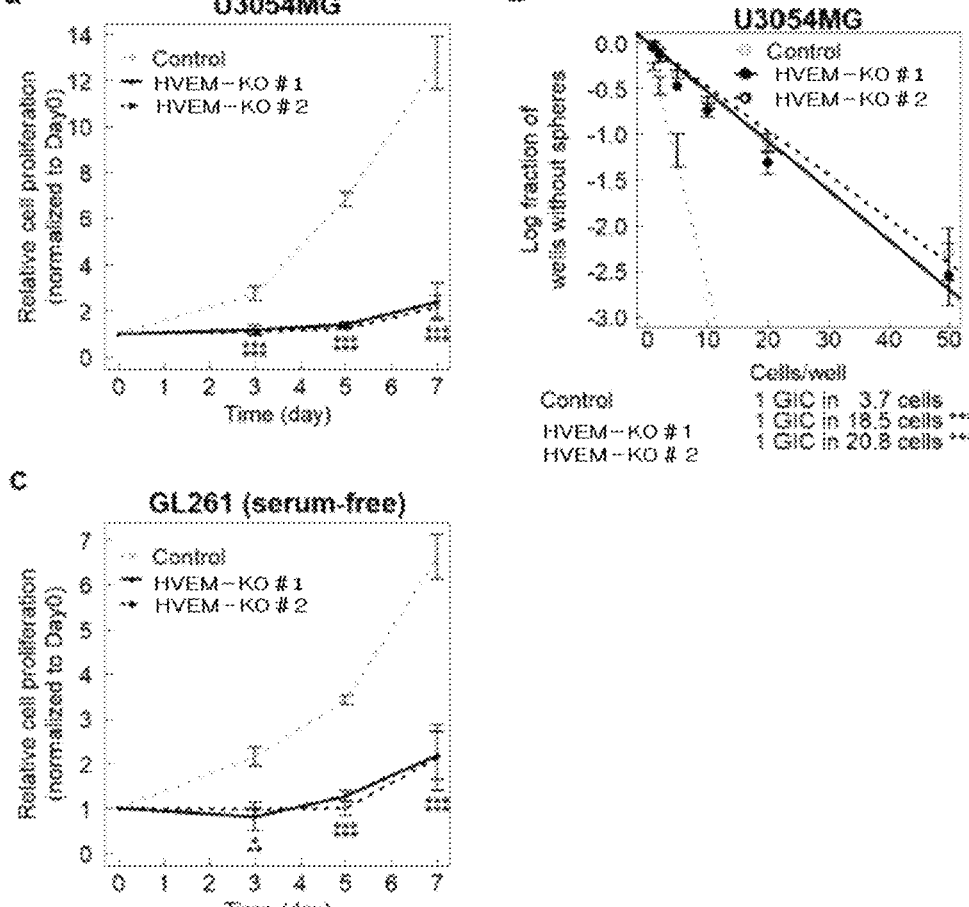
FIG. 12 is a diagram showing an influence of knockout (KO) of the HVEM gene by genome editing in Example 11. (a) A diagram showing that the proliferation of the mesenchymal subtype cells is inhibited in cell culture by human HVEM gene knockout. Data is indicated as mean±SD (n=4 biological replicates for a cell proliferation assay; P<0.01, *P<0.001; two-tailed unpaired Student's t-test with Bonferroni correction). (b) A diagram showing that the neurosphere formation of the mesenchymal subtype cells is inhibited in cell culture by human HVEM gene knockout. Data is indicated as mean±SD (n=3 biological replicates for a cell proliferation assay; P<0.01, *P<0.001; two-way analysis of variance with Bonferroni correction). (c) A diagram showing that cell proliferation is inhibited in cell culture by mouse HVEM gene (Tnfrsfl4) knockout. Data is indicated as mean±SD (n=3; *P<0.01, P<0.01, *P<0.001; two-tailed unpaired Student's t-test with Bonferroni's correction).

The results were as shown in FIG. 12. Knockout of the HVEM gene by the CRISPR/Cas9 system was confirmed to strongly reduce the proliferation of the mesenchymal subtype cell strain (FIG. 12a). In addition, the sphere formation ability of the mesenchymal subtype cells was suppressed by knockout of the HVEM gene (FIG. 4b). In addition, the murine glioma cell strain GL261 cells are cells showing an increased HVEM expression when cultured without serum (see Example 7), and cell proliferation was confirmed to be attenuated by knockout of the mouse HVEM gene also in these cells (FIG. 12c).

Figure 13:
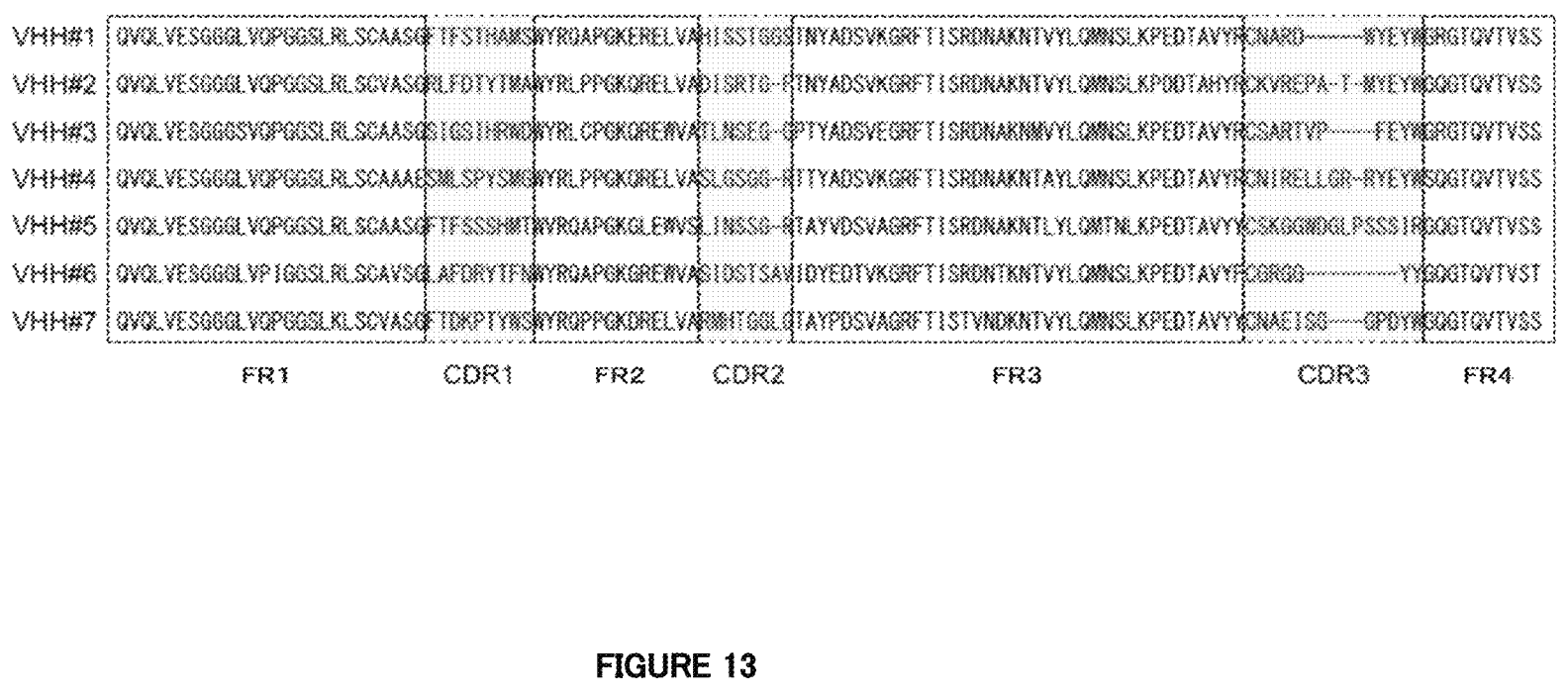

Example 12: Preparation of HVEM Antibody Using Alpaca (1) Preparation of Antibody in Alpaca HEK293T cells expressing a human HVEM gene (GenBank Accession No. NM_003820.3 or HGNC:11912) were immunized under the skin of an alpaca to prepare an anti-human HVEM alpaca VHH antibody. VHH antibodies having the amino acid sequences indicated in Table 9 were obtained. The complementarity determining regions (CDRs) were identified according to Kabat's classification. The results were as shown in FIG. 13.

[Table 9]

TABLE 9

Amino acid sequence of anti-human HVEM alpaca VHH antibody

| VHH antibody No. | | SEQ ID NO: |
|---|---|---|
| #1 | QVQLVESGGGLVQPGGSLRLSCAASGFTFSTHAMSWYRQ APGKERELVAHISSTGGSTNYADSVKGRFTISRDNAKNT VYLQMNSLKPEDTAVYRCNARDWYEYWGRGTQVTVSS | 29 |
| #2 | QVQLVESGGGLVQPGGSLRLSCVASGRLFDTYTMAWYRL PPGKQRELVADISRTGFTNYADSVKGRFTISRDNAKNTV YLQMNSLKPDDTAHYRCKVREPATMYEYWGQGTQVTVSS | 30 |
| #3 | QVQLVESGGGSVQPGGSLRLSCAASGSIGSIHRWDWYRL CPGKQREWVATLNSEGGPTYADSVEGRFTISRDNAKNMV YLQMNSLKPEDTAVYRCSARTVPFEYWGRGTQVTVSS | 31 |

TABLE 9-continued

Amino acid sequence of anti-human HVEM
alpaca VHH antibody

| VHH antibody No. | | SEQ ID NO: |
|---|---|---|
| #4 | QVQLVESGGGLVQPGGSLRLSCAAAESMLSPYSMGWYRL PPGKQRELVASLGSGGRTTYADSVKGRFTISRDNAKNTA YLQMNSLKPEDTAVYRCNIRELLGRRYEYWSQGTQVTVS S | 32 |
| #5 | QVQLVESGGGLVQPGGSLRLSCAASGFTFSSSHMTWVRQ APGKGLEWVSLINSSGRTAYVDSVAGRFTISRDNAKNTL YLQMTNLKPEDTAVYYCSKGGWDGLPSSSIRGQGTQVTV SS | 33 |
| #6 | QVQLVESGGGLVPIGGSLRLSCAVSGLAFDRYTFNWYRQ APGKGREWVASIDSTSAVIDYEDTVKGRFTISRDNTKNT VYLQMNSLKPEDTAVYFCGRGGYYGQGTQVTVST | 34 |
| #7 | QVQLVESGGGLVQPGGSLKLSCVASGFTDKPTYWSWYRQ PPGKDRELVARMHTGGLGTAYPDSVAGRFTISTVNDKNT VYLQMNSLKPEDTAVYYCNAEISGGPDYWGQGTQVTVSS | 35 |

(2) Binding of HVEM Antibody to Antigen

The VHH antibodies prepared in the above item (1) were used to measure whether the VHH antibodies were detected in HVEM on the surface of the HVEM-expressing HEK293T cell membrane. Specifically, the HEK293T cells introduced with HVEM and the HEK293T cells not expressing HVEM as a negative control were each seeded at $1\times10^4$ cells/well, fixed with 4% paraformaldehyde, and then reacted with the VHH antibodies added with 6×His tag. The horseradish peroxidase HRP-labeled anti-histidine tag antibody anti-His-tag mAb-HRP-DirecT (MBL) was reacted, and ELISA POD Substrate TMB Kit (Nacalai Tesque, Inc.) was used to measure an enzyme reaction of HRP with the substrate. The effect size data obtained for the antibody concentration was subjected to non-linear regression to a sigmoid curve based on the following formula:

$$\text{Effect size} = \text{background} + \text{maximum effect size}/(1+10^{\wedge}$$
$$(\text{Hill coefficient}\times(\log EC50\text{-log(antibody concentration)})))$$

to determine the 50% effect concentration EC50.

As a result, the EC50 values of VHH #1 to 5 were all less than 80 nM. Clones of VHH #6 and VHH #7 were obtained by antibody screening using the phage display method.

(3) Proliferation Inhibitory Effect of VHH Antibody

Figure 14:
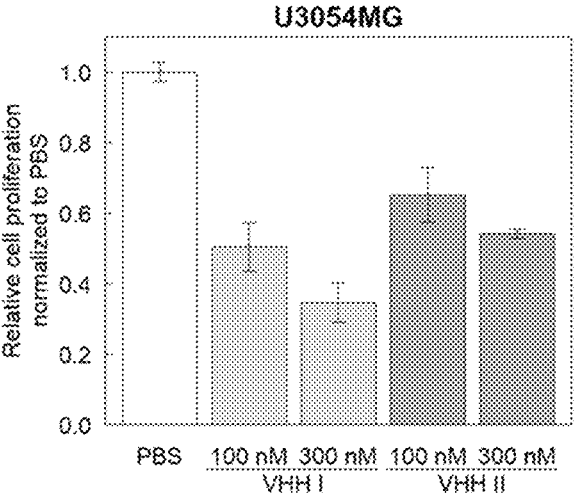
FIG. 14 is a diagram showing an influence of an anti-human HVEM antibody on proliferation of the mesenchymal subtype cells in Example 12. Data is indicated as mean±SD (n=2 biological replicates).

The mesenchymal subtype cell strain (U3054MG cells) was treated with VHH(I) (VHH #3) and VHH(II) (VHH #2) at a concentration of 100 to 300 nM, and the U3054MG cells were cultured under the conditions: 37° C. and 5% CO2 for 7 days. As a negative control, the cell strain was treated with PBS. Cell proliferation was quantified using Cell Count Reagent SF (Nacalai Tesque, Inc.) to measure cell proliferation for the PBS-treated group. The results were as shown in FIG. 14. Proliferation was shown to be suppressed in the VHH-treated cells.

What is claimed is:

1. A single variable domain of an immunoglobulin heavy chain which binds to herpesvirus entry mediator (HVEM), said domain comprising a polypeptide with an amino acid sequence having at least 80% identity to the amino acid sequence of any of SEQ ID NOs: 30 to 35 or having at least 85% identity to the amino acid sequence of SEQ ID NO: 29.

2. The single variable domain of the heavy chain according to claim 1, which comprises complementarity determining regions 1 to 3 (CDR1, CDR2 and CDR3), wherein amino acid sequences of CDR1 CDR2 and CDR3 are the following (i), (ii), (iii), (iv), (v), (vi) or (vii):

(i) CDR1 comprising an amino acid sequence represented by SEQ ID NO: 36, CDR2 comprising an amino acid sequence represented by SEQ ID NO: 37, and CDR3 comprising an amino acid sequence represented by SEQ ID NO: 38:

(ii) CDR1 comprising an amino acid sequence represented by SEQ ID NO: 39, CDR2 comprising an amino acid sequence represented by SEQ ID NO: 40, and CDR3 comprising an amino acid sequence represented by SEQ ID NO: 41, (iii) CDR1 comprising an amino acid sequence represented by SEQ ID NO: 42, CDR2 comprising an amino acid sequence represented by SEQ ID NO: 43, and CDR3 comprising an amino acid sequence represented by SEQ ID NO: 44;

(iv) CDR1 comprising an amino acid sequence represented by SEQ ID NO: 45, CDR2 comprising an amino acid sequence represented by SEQ ID NO: 46, and CDR3 comprising an amino acid sequence represented by SEQ ID NO: 47;

(v) CDR1 comprising an amino acid sequence represented by SEQ ID NO: 48, CDR2 comprising an amino acid sequence represented by SEQ ID NO: 49, and CDR3 comprising an amino acid sequence represented by SEQ ID NO: 50;

(vi) CDR1 comprising an amino acid sequence represented by SEQ ID NO: 51, CDR2 comprising an amino acid sequence represented by SEQ ID NO: 52, and CDR3 comprising an amino acid sequence represented by SEQ ID NO: 53; or (vii) CDR1 comprising an amino acid sequence represented by SEQ ID NO: 54, CDR2 comprising an amino acid sequence represented by SEQ ID NO: 55, and CDR3 comprising an amino acid sequence represented by SEQ ID NO: 56.

3. The single variable domain of the heavy chain according to claim 2, which comprises framework regions (FR1, FR2, FR3 and FR4), wherein amino acid sequences of FR1, FR2, FR3 and FR4 are the following (viii), (ix), (x), (xi), (xii), (xiii) or (xiv):

(viii) FR1 comprising an amino acid sequence represented by SEQ ID NO: 57, FR2 comprising an amino acid sequence represented by SEQ ID NO: 58, FR3 comprising an amino acid sequence represented by SEQ ID NO: 59, and FR4 comprising an amino acid sequence represented by SEQ ID NO: 60;

(ix) FR1 comprising an amino acid sequence represented by SEQ ID NO: 61, FR2 comprising an amino acid sequence represented by SEQ ID NO: 62, FR3 comprising an amino acid sequence represented by SEQ ID NO: 63, and FR4 comprising an amino acid sequence represented by SEQ ID NO: 64;

(x) FR1 comprising an amino acid sequence represented by SEQ ID NO: 65, FR2 comprising an amino acid sequence represented by SEQ ID NO: 66, FR3 comprising an amino acid sequence represented by SEQ ID NO: 67, and FR4 comprising an amino acid sequence represented by SEQ ID NO: 68;

(xi) FR1 comprising an amino acid sequence represented by SEQ ID NO: 69, FR2 comprising an amino acid sequence represented by SEQ ID NO: 70, FR3 comprising an amino acid sequence represented by SEQ ID NO: 71, and FR4 comprising an amino acid sequence represented by SEQ ID NO: 72;

(xii) FR1 comprising an amino acid sequence represented by SEQ ID NO: 73, FR2 comprising an amino acid sequence represented by SEQ ID NO: 74, FR3 comprising an amino acid sequence represented by SEQ ID NO: 75, and FR4 comprising an amino acid sequence represented by SEQ ID NO: 76;

(xiii) FR1 comprising an amino acid sequence represented by SEQ ID NO: 77, FR2 comprising an amino acid sequence represented by SEQ ID NO: 78, FR3 comprising an amino acid sequence represented by SEQ ID NO: 79, and FR4 comprising an amino acid sequence represented by SEQ ID NO: 80; or (xiv) FR1 comprising an amino acid sequence represented by SEQ ID NO: 81, FR2 comprising an amino acid sequence represented by SEQ ID NO: 82, FR3 comprising an amino acid sequence represented by SEQ ID NO: 83, and FR4 comprising an amino acid sequence represented by SEQ ID NO: 84.

4. An antibody or an immunoglobulin multimer, each having variable regions consisting of single variable domains of the heavy chain according to claim 1.

5. A polynucleotide encoding the single variable domain of the heavy chain according to claim 1 or the antibody or multimer according to claim 4.

6. A pharmaceutical composition comprising the single variable domain of the heavy chain according to claim 1 or the antibody or multimer according to claim 4.

7. The pharmaceutical composition according to claim 6, which is formulated for the treatment of a glioma.

* * * * *